US007166684B2

(12) United States Patent
Seki et al.

(10) Patent No.: US 7,166,684 B2
(45) Date of Patent: Jan. 23, 2007

(54) TRANSITION METAL COMPOUND, CATALYST FOR OLEFIN POLYMERIZATION AND METHOD FOR PRODUCING POLYOLEFIN

(75) Inventors: Takashi Seki, Yokohama (JP); Hiroyuki Shimizu, Tokyo (JP); Tamotsu Takahashi, Sapporo (JP); Kiyohiko Nakajima, Okazaki (JP); Tetsuro Fukuda, Kawasaki (JP)

(73) Assignee: Japan Polyethylene Corporation, Tokyo (JP)

( * ) Notice: Subject to any disclaimer, the term of this patent is extended or adjusted under 35 U.S.C. 154(b) by 15 days.

(21) Appl. No.: 10/525,929

(22) PCT Filed: Oct. 24, 2003

(86) PCT No.: PCT/JP03/13610

§ 371 (c)(1),
(2), (4) Date: Feb. 25, 2005

(87) PCT Pub. No.: WO2004/037841

PCT Pub. Date: May 6, 2004

(65) Prior Publication Data
US 2006/0167196 A1    Jul. 27, 2006

(30) Foreign Application Priority Data
Oct. 25, 2002    (JP) .............................. 2002-311451

(51) Int. Cl.
C08F 4/76 (2006.01)
C08F 4/72 (2006.01)
B01J 31/38 (2006.01)
C07F 17/00 (2006.01)

(52) U.S. Cl. ..................... 526/170; 526/160; 526/943; 526/941; 502/103; 556/53; 556/52; 556/51

(58) Field of Classification Search ................ 526/943, 526/170, 941, 160, 53, 51
See application file for complete search history.

(56) References Cited

U.S. PATENT DOCUMENTS 5,324,800 A * 6/1994 Welborn et al. ............ 526/160
6,043,180 A * 3/2000 Jacobsen et al. ............ 502/103
6,150,544 A * 11/2000 Seki et al. ..................... 556/27
6,486,277 B1   11/2002 Erker et al.

OTHER PUBLICATIONS

Kopf et al. Cryst. Struct. Comm., 1980, 9, 985-990.*
Brackemeyer et al. Organometallics 1997, 16,531-536.*
Edelbach et al. Organometallics 1999, 18, 3170-3177.*
Lukens et al. Organometallics 1995, 14, 3435-3439.*
Schmid et al. J. Organomet. Chem. 1997, 544(1), 139-142 (abstract).*
Sinn et al. Angew. Chem., 1980, 5, 396-402.*
Sinn, Hansjoerg, et al., "Living polymers" with Ziegler catalysts of high productivity Angewandte Chemie, 1980, vol. 92, No. 5, pp. 396-402.

* cited by examiner

*Primary Examiner*—Ling-Sui Choi
*Assistant Examiner*—Rip A. Lee
(74) *Attorney, Agent, or Firm*—Scully, Scott, Murphy & Presser, PC

(57) ABSTRACT

A novel transition metal compound wherein the transition metal belongs to group 4 of the periodic table and the transition metal compound has a hydrogen atom ligand and three cyclopentadienyl ligands comprising at least one substituted cyclopentadienyl ligand. The novel transition metal compound can be used as a component of a catalyst exhibiting high activity for olefin polymerization and is characteristic in containing no halogen element.

17 Claims, 2 Drawing Sheets

TRANSITION METAL COMPOUND, CATALYST FOR OLEFIN POLYMERIZATION AND METHOD FOR PRODUCING POLYOLEFIN

TECHNICAL FIELD

This invention relates to a novel transition metal compound, a catalyst for olefin polymerization, and a method for producing polyolefin.

BACKGROUND ART

Many compounds composed of transition metals of group 4 of the periodic table and cyclopentadienyl ligands or substituted cyclopentadienyl ligands, which are coordinating to the transition metal, have been synthesized. As well known in the prior art, these compounds are used for various organic syntheses such as catalysts for polymerization. (e.g., SYNTHESIS, Jan. 1988, 1–19 and Japanese Patent Laid-Open Publication No. S58-19309). It is disclosed that the density and molecular weight of the polymer can be changed in olefin-copolymerization by introducing substituted group into the cyclopentadienyl ligand of transition metal compound. (Japanese Patent Publication No. H7-37488, etc.)

However, most of these transition metal compounds are mono-cyclopentadienyl compounds, mono-substituted cyclopentadienyl compounds, biscyclopentadienyl compounds and bis-substituted cyclopentadienyl compounds.

There are hitherto several reports concerning triscyclopentadienyl compounds and tris-substituted cyclopentadienyl compounds. They are exemplified by $Cp_3ZrCl$ (Bul. Chem. Soc. Fr., 1978, II-292), $Cp_3ZrMe$ (Organometallics 1997, 16, 531), $(MeCp)_3ZrCl$ (Bul. Chem. Soc. Fr., 1978, II-292), $(Me_3SiCp)_3ZrCl$ (Acta. Cryst., 1995, C51, 10) and $Ind_3MCl$ (M=Zr, Hf) (J. Organomet. Chem., 1997, 544, 139). The number of information of this kind is not large.

Concerning the triscyclopentadienyl metal hydride compounds and tris-substituted cyclopentadienyl metal hydride compounds (the metal is a transition metal of group 4 of the periodic table), only $CP_3ZrH$ has been hitherto reported. (The structural analyses by IR spectrometry and Raman spectrometry are reported in J. Organomet. Chem., 1982, 235, 69 and the structural analysis by X-ray diffractiometry is reported in Organometallics, 1999, 18, 3170.) Concerning the method for synthesizing these compounds, only the reactions of $LiAlH_4$ with $Cp_4Zr$ and t-BuLi with $Cp_4Zr$ are known. In addition to these reactions, the reaction of $LiAlH_4$ with $Cp_3ZrCl$ and the reaction of alkyl lithium with $CP_3ZrCl$ are considered. However, intended compounds are hardly obtained through these reactions because of the occurrence of a side-reaction to lose Cp ligand. Concerning the tetrakis-cyclopentadienyl zirconium compound which has at least one substituted cyclopentadienyl group other than cyclopentadienyl group, the report is hardly found because the repulsion by steric hindrance is largely caused to occur.

In other words, any transition metal compound having at least one-substituted cyclopentadienyl group among its three cyclopentadienyl ligands has not been known at all.

The mono-cyclopentadienyl metal compound, bis-cyclopentadienyl metal compound and triscyclopentadienyl metal compound are generally stable as halogenides such as chlorides (the metal is a transition metal of group 4 of the periodic table). The polyolefin that is polymerized in the presence of the catalyst of these compounds, contains a trace amount of halogen compound resulted from the catalyst. The polyolefin containing halogen compound, even when the amount is very small, is liable to be oxidized by heat or light rays and yellowing is caused to occur, so that antioxidant or halogen catcher is often used.

With the increasing tendency to the prevention of environmental problem in recent years, the polyolefin containing no additives such as halogen compound or antioxidant, which gives undesirable influence to human body, is largely demanded. Particularly, in the fields of food packages and medical appliances, the halogen-free or additive-free polyolefin is in great demand. As the metal compounds containing no halogen element, in which the metal is a transition metal of group 4 of the periodic table, there are exemplified by mono-cyclopentadienyl metal alkyl compound and bis-cyclopentadienyl metal alkyl compound. These compounds can be prepared from corresponding halogenides by using Grignard reagent or alkyl lithium.

Among these compounds, however, most of these compounds having hydrogen atom at β-position are not stable owing to the occurrence of release of β-hydrogen atom. Meanwhile, the compounds having no hydrogen atom at β-position, such as methylated compounds and benzyl compounds can exist as thermodynamically stable compounds because they are free from the releasing of the hydrogen atom at β-position. However, these alkyl compounds must be stored strictly in an inert gas atmosphere, because the compounds are liable to react with water or oxygen in the system to decompose even when the content of water or oxygen is very small. In order to synthesize the alkyl compound from tris-cyclopentadienyl metal halide, when the alkylation is carried out by using Grignard reagent or alkyl lithium, which is used in ordinary synthesizing method for complexes, the reaction to release one cyclopentadienyl ligand from the three ligands occurs. Accordingly, it is difficult to synthesize the alkyl compound at high yield through this method.

The present invention provides a novel transition metal compound, which has not been known yet. This novel transition metal compound can be an excellent catalyst exhibiting high polymerizing activity when it is used as a component of catalyst for olefin polymerization. The new metal compound contains no halogen element, so that the obtained polyolefin contains no halogen element. Accordingly, the amount of additives can be reduced as compared with conventional polyolefin. In addition, the polyolefin can also be used without adding any additive. The novel transition metal compound is composed of a transition metal of group 4 of the periodic table, three ligands of cyclopentadienyl derivative and one hydrogen atom. The transition metal compound of this kind has never been known. Furthermore, it has not been known either that the transition metal compound can be used as a component of catalyst for olefin polymerization.

The novel transition metal compound according to the present invention is a compound of a metal of group 4 of the periodic table having ligands of three cyclopentadienyl derivatives and one hydrogen atom, which compound contains no halogen element. The transition metal compound of this invention is more stable in relation to water and oxygen, as compared with the dialkylmetallocene of the same metal.

DISCLOSURE OF INVENTION

This invention provides a novel transition metal compound, which can be used as a component of high activity catalyst for polymerization of olefin containing no halogen element. The compound is composed of a transition metal of group 4 of the periodic table having three cyclopentadienyl ligands and a ligand of hydrogen atom. At least one of the three cyclopentadienyl ligands is a substituted cyclopentadienyl group.

The invention will be described in more detail.

The novel transition metal compound of a first aspect of the present invention is represented by the following general formula (1).

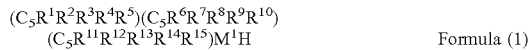
Formula (1)

[In the formula, $(C_5R^1R^2R^3R^4R^5)$, $(C_5R^6R^7R^8R^9R^{10})$ and $(C_5R^{11}R^{12}R^{13}R^{14}R^{15})$ denote a cyclopentadienyl group or a substituted cyclopentadienyl group, respectively. $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are any one of hydrogen atom, hydrocarbon group having 1 to 30 carbon atoms or organosilicon group having substituent group of hydrocarbon having 1 to 30 carbon atoms, which can be the same or different from one another. Any of $R^1$, $R^2$, $R^3$, $R^4$ and $R^5$; or $R^6$, $R^7$, $R^8$, $R^9$ and $R^{10}$; or $R^{11}R^{12}$, $R^{13}R^{14}$ and $R^{15}$ can be bonded to one another forming a cyclic hydrocarbon group (including polycyclic structure). However, at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ must be a substituent group other than a hydrogen atom. $M^1$ denotes a transition metal of group 4 of the periodic table.]

The transition metal compound of a second aspect of the present invention is represented by the following general formula (2).

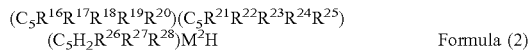
Formula (2)

[In the formula, $C_5R^{16}R^{17}R^{18}R^{19}R^{20}$, $C_5R^{21}R^{22}R^{23}R^{24}R^{25}$ and $C_5R_2R^{26}R^{27}R^{28}$ denote a cyclopentadienyl group or a substituted cyclopentadienyl group respectively. $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are any one of a hydrogen atom, a hydrocarbon group having 1 to 30 carbon atoms or an organosilicon group having substituent of a hydrocarbon having 1 to 30 carbon atoms, which can be the same or different from each other. Among them, any group of $R^{16}$, $R^{17}$, $R^{18}$, $R^{19}$ and $R^{20}$; or $R^{21}$, $R^{22}$, $R^{23}$, $R^{24}$ and $R^{25}$; or $R^{26}$, $R^{27}$ and $R^{28}$ can be bonded to each other forming a cyclic hydrocarbon group (including polycyclic structure). At least one of $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ must be a substituent group other than a hydrogen atom. $M^2$ denotes a transition metal of group 4 of the periodic table.]

The transition metal compound of a third aspect of the present invention is represented by the foregoing general formula (2), wherein $R^{26}$, $R^{27}$ and $R^{28}$ are bonded to adjacent carbon atoms of 1-position, 2-position and 3-position of the transition metal compound.

The transition metal compound of a fourth aspect of the present invention is represented by the following general formula (3).

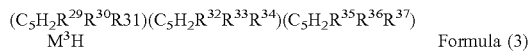
Formula (3)

[In the formula, $(C_5H_2R^{29}R^{30}R^{31})$, $(C_5H_2R^{32}R^{33}R^{34})$ and $(C_5H_2R^{35}R^{36}R^{37})$ denote a cyclopentadienyl group or a substituted cyclopentadienyl group, respectively. The symbols $R^{29}$, $R^{30}$, $R^{31}$, $R^{32}$, $R^{33}$, $R^{34}$, $R^{36}$ and $R^{37}$ are any of a hydrogen atom, a hydrocarbon group having 1 to 30 carbon atoms or an organosilicon group having a substituent of hydrocarbon having 1 to 30 carbon atoms, which may be same or different from one another. Furthermore, $R^{29}$, $R^{30}$ and $R^{31}$; or $R^{32}$, $R^{33}$ and $R^{34}$, or $R^{35}$, $R^{36}$ and $R^{37}$ can be bonded to one another to form a cyclic hydrocarbon group (including polycyclic structure), however, at least one of $R^{29}$, $R^{30}$, $R^{31}$, $R^{32}$, $R^{33}$, $R^{34}$, $R^{35}$, $R^{36}$ and $R^{37}$ must be a substituent group other than a hydrogen atom. The symbol $M^3$ denotes a transition metal of group 4 of the periodic table.]

The transition metal compound of a fifth aspect of the present invention is represented by the foregoing general formula (3), wherein the groups of $R^{29}$, $R^{30}$ and $R^{31}$; $R^{32}$, $R^{33}$ and $R^{34}$; and $R^{35}$, $R^{36}$ and $R^{37}$ are bonded to adjacent carbon atoms of 1-position, 2-position and 3-position of the respective cyclopentadienyl group.

The transition metal compound of a sixth aspect of the present invention is represented by the foregoing general formula (3), wherein the three substituted cyclopentadienyl groups of $(C_5H_2R^{29}R^{30}R^{31})$, $(C_5H_2R^{32}R^{33}R^{34})$ and $(C_5H_2R^{35}R^{36}R37)$, are same.

The transition metal compound of a seventh aspect of the present invention is represented by the following general formula (4).

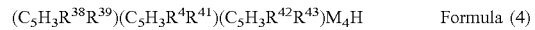
Formula (4)

[In the formula, the groups of $(C_5H_3R^{38}R^{39})$, $(C_5H_3R^{40}R^{41})$ and $(C_5H_3R^{42}R^{43})$ denote cyclopentadienyl groups or substituted cyclopentadienyl groups, respectively. The groups of $R^{38}$, $R^{39}$, $R^{40}$, $R^{41}$, $R^{42}$ and $R^{43}$ are a hydrogen atom, a hydrocarbon group having 1 to 30 carbon atoms or an organosilicon group having a substituent of hydrocarbon having 1 to 30 carbon atoms, which may be the same or different from one another. Any of $R^{38}$, $R^{39}$; or $R^{40}$, $R^{41}$; or $R^{42}$, $R^{43}$ can be bonded to each other forming a cyclic hydrocarbon group (including polycyclic structure). At least one of $R^{38}$, $R^{39}$, $R^{40}$, $R^{41}$, $R^{42}$ and $R^{43}$ is a substituent other than a hydrogen atom. The symbol $M^4$ denotes a transition metal of group 4 of the periodic table.]

The transition metal compound of an eighth aspect of the present invention is represented by the foregoing general formula (4), wherein the three substituted cyclopentadienyl groups of $(C_5H_3R^{38}R^{39})$, $(C_5H_3R^{40}R^{41})$ and $(C_5H_3R^{42}R^{43})$, are the same in structures.

The transition metal compound of a ninth aspect of the present invention is represented by the following general formula (5).

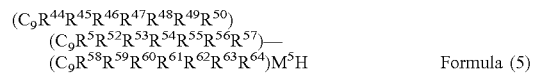
Formula (5)

[In the formula, $(C_9R^{44}R^{45}R^{46}R^{47}R^{48}R^{49}R^{50})$, $(C_9R^{51}R^{52}R^{53}R^{54}R^{55}R^{56}R^{57})$ and $(C_9R^{58}R59R^{60}R^{61}R^{62}R^{63}R^{64})$ denote an indenyl group or a substituted indenyl group, respectively. The groups of R44 to $R^{64}$ are any one of a hydrogen atom, a hydrocarbon group having 1 to 30 carbon atoms or an organosilicon group having a substituent of hydrocarbon having 1 to 30 carbon atoms, which can be the same or different from one another. Any group of $R^{44}$ to $R^{50}$; $R^{51}$ to $R^{57}$ and $R^{58}$ to $R^{64}$ may be bonded to one another forming a cyclic hydrocarbon group (including polycyclic structure). At least one of $R^{38}$, $R^{39}$, $R^{40}$, $R^{41}$, $R^{42}$ and $R^{43}$ must be a substituent other than hydrogen atom. The symbol $M^5$ denotes a transition metal of group 4 of the periodic table.]

The transition metal compound of a tenth aspect of the present invention is represented by the following general formula (6).

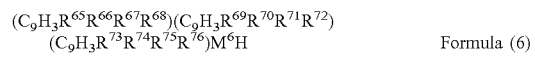
Formula (6)

[In the formula, the groups of $(C_9H_3R^{65}R^{66}R^{67}R^{68})$, $(C_9H_3R^{69}R^{70}R^{71}R^{72})$ and $(C_9H_3R^{73}R^{74}R^{75}R^{76})$ denote indenyl groups or substituted indenyl groups, respectively. $R^{65}$ to $R^{76}$ are any one of a hydrogen atom, a hydrocarbon group having 1 to 30 carbon atoms or an organosilicon group having a substituent of hydrocarbon having 1 to 30 carbon atoms, which may be the same or different from one another. Among them, $R^{65}$ to $R^{68}$; $R^{69}$ to $R^{72}$ and $R^{73}$ to $R^{76}$ can be bonded to the carbon atoms of 4-position, 5-position, 6-position and 7-position (positions of six-membered ring) of the respective indenyl groups to form cyclic hydrocarbon groups (including polycyclic structure). The symbol $M^6$ denotes a transition metal of group 4 of the periodic table.]

The transition metal compound of an eleventh aspect of the present invention is represented by the foregoing general formula (6), wherein the three substituted indenyl groups of $(C_9H_3R^{65}R^{66}R^{67}R^{68})$, $(C_9H_3R^{69}R^{70}R^{71}R^{72})$ and $(C_9H_3R^{73}R^{74}R^{75}R^{76})$, are the same in structure.

The transition metal compound of a twelfth aspect of the present invention is represented by any one of the foregoing general formulae (1) to (6), wherein the transition metal of group 4 of the periodic table is Zr.

The catalyst for use in olefin polymerization in the present invention is composed of any one of the transition metal compounds described in the foregoing first to twelfth aspects, an organoaluminum oxy compound and/or a compound which can form an ion pair with the transition metal compound.

The second catalyst for olefin polymerization in the present invention is the one in which the above-mentioned organoaluminum oxy compound is methyl aluminoxane.

The third catalyst for olefin polymerization in the present invention is a solid catalyst, which is prepared by supporting the foregoing catalyst on a carrier.

The fourth catalyst for olefin polymerization in the present invention is a solid catalyst, in which any one of the transition metal compounds described in the forgoing first to twelfth aspects is supported on layered silicate.

The method for producing polyolefin of the present invention is a polymerizing method, in which olefin is polymerized in the presence of any one of the catalyst for olefin polymerization as described above.

The second aspect of the method for producing polyolefin of the present invention is a polymerizing method, in which the foregoing olefin polymerization is homopolymerization of ethylene or copolymerization of ethylene and α-olefin.

The transition metal compounds of the present invention will be described in more detail.

In the transition metal compound in the general formula (1) of the invention, each of $C_5R^1R^2R^3R^4R^5$, $C^5R^6R^7R^8R^9R^{10}$ and $C_5R^{11}R^{12}R^{13}R^{14}R^{15}$ denotes a cyclopentadienyl group or a substituted cyclopentadienyl group. Each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ is any one of a hydrogen atom, a hydrocarbon group having 1 to 30 carbon atoms or an organosilicon group having a substituent of hydrocarbon having 1 to 30 carbon atoms, which can be the same or different from one another. The number of carbon atoms is preferably 1 to 24, and more preferably 1 to18. Any of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ can be bonded to one another to form a cyclic hydrocarbon group (including polycyclic structure), provided that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ must be a substituent group other than hydrogen atom.

The hydrocarbon groups of $R^1$, $R^2$, $R^3$, $R^4$, $R^5$, $R^6$, $R^7$ $R^8$ $R^9$, $R^{10}$, $R^{11}$, $R^{12}$, $R^{13}$, $R^{14}$ and $R^{15}$ are exemplified by alkyl groups such as methyl group, ethyl group, propyl group, butyl group, pentyl group, hexyl group and cyclohexyl group; alkenyl groups such as vinyl group and allyl group; aryl groups such as phenyl group, dimethylphenyl group, diethylphenyl group, dipropylphenyl group, dibutylphenyl group, trimethylphenyl group, triethylphenyl group, tripropylphenyl group, tributylphenyl group, biphenyl group, naphthyl group and anthryl group; and arylalkyl groups such as trityl group, phenethyl group, styryl group, benzhydryl group, phenylpropyl group, phenylbutyl and neophyl group. These groups may be branched structure.

As more particular examples, there are methyl group, ethyl group, propyl group, butyl group, cyclohexyl group, vinyl group, allyl group and phenyl group. Among these groups, methyl group, ethyl group, propyl group, butyl group and phenyl group are more preferable.

The organosilicon groups having substituent of hydrocarbon with 1 to 30 carbon atoms of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are exemplified by alkylsilyl groups having substituent of alkyl group such as methyl group, ethyl group, propyl group, butyl group, pentyl group, hexyl group and cyclohexyl group; alkenylsilyl groups having substituent of alkenyl group such as vinyl group and allyl group; arylsilyl groups having substituent of aryl group such as phenyl group, dimethylphenyl group, diethylphenyl group, dipropylphenyl group, dibutylphenyl group, trimethyl-phenyl group, triethylphenyl group, tripropylphenyl group, tributylphenyl group, biphenyl group, naphthyl group and anthryl group; and arylalkylsilyl groups having substituent of arylalkyl group such as trityl group, phenethyl group, styryl group, benzhydryl group, phenylpropyl group, phenylbutyl group and neophyl group. These groups can have a branched chain.

They are exemplified more particularly by trimethylsilyl group, triethylsilyl group, tripropylsilyl group, tributylsilyl group, trivinylsilyl group, triallylsilyl group and triphenylsilyl group. Among them, trimethylsilyl group, triethylsilyl group and triphenylsilyl group are more preferable.

The groups of $R^1$, $R^2$, $R^3$, $R^4$ and $R^5$; or $R^6$, $R^7$, $R^8$, $R^9$ and $R^{10}$; or $R^{11}$, $R^{12}$, $R^{13}$, $R^{14}$ and $R^{15}$ can be bonded to one another, especially to adjacent group to form a cyclic hydrocarbon group (including polycyclic structure). $(C_5R^1R^2R^3R^4R^5)$, $(C_5R^6R^7R^8R^9R^{10})$ and $(C_5R^{11}R^{12}R^{13}R^{14}R^{15})$ as the cyclic hydrocarbon groups (including polycyclic structure) that are formed by the bonding are exemplified by indenyl group; alkylindenyl group having one or more alkyl groups such as methyl group, ethyl group, propyl group, butyl group, pentyl group, hexyl group or cyclohexyl group; alkenylindenyl group having one or more alkenyl group such as vinyl group or allyl group; arylindenyl group having one or more aryl group such as phenyl group, dimethylphenyl group, diethylphenyl group, dipropylphenyl group, dibutyl-phenyl group, trimethylphenyl group, triethylphenyl group, tripropylphenyl group, tributylphenyl group, biphenyl group, naphthyl group or anthryl group; arylalkylindenyl group having one or more arylalkyl group such as trityl group, phenethyl group, styryl group, benzhydryl group, phenylpropyl group, phenylbutyl or neophyl group; tetrahydroindenyl group; benzoindenyl group having polycyclic structure, wherein the benzoindenyl group is the one having the structure represented by the following structural formula (1) or (2), and the same being applied to the description hereinafter; alkylbenzoindenyl groups having one or more alkyl group such as methyl group, ethyl group, propyl group, butyl group, pentyl group, hexyl group or cyclohexyl group; alkenylbenzoindenyl groups having one or more alkenyl group such as vinyl group or allyl group; arylbenzoindenyl groups having one or more of aryl group such as phenyl group, dimethylphenyl group, diethylphenyl group, dipropylphenyl group, dibutylphenyl group, trimethyl-phenyl group, triethylphenyl group, tripropylphenyl group, tributylphenyl group, biphenyl group, naphthyl group or anthryl group; arylalkyl-benzoindenyl groups having one or more arylalkyl group such as trityl group, phenethyl group, styryl group, benzhydryl group, phenylpropyl group, phenylbutyl group or neophyl group; dibenzoindenyl group having polycyclic structure, wherein the dibenzoindenyl group is the one having the structure represented by the following. structural formula (3). The same is applied to the description hereinafter; alkyldibenzoindenyl groups having one or more alkyl group such as methyl group,- ethyl group, propyl group, butyl group, pentyl group, hexyl group or cyclohexyl group; alkenyl-dibenzoindenyl groups having one or more alkenyl group such as vinyl group or allyl group; aryldibenzoindenyl groups having one or more aryl group such as phenyl group, dimethylphenyl group, diethylphenyl group, dipropylphenyl group, dibutylphenyl group, trimethylphenyl group, triethylphenyl group, tripropylphenyl group, tributylphenyl group, biphenyl group, naphthyl group or anthryl group; arylalkyldibenzoindenyl groups having one or more arylalkyl group such as trityl group, phenethyl group, styryl group, benzhydryl group, phenylpropyl group, phenylbutyl group or neophyl group; azulenyl group; alkylazulenyl group having one or more alkyl group such as methyl group, ethyl group, propyl group, butyl group, pentyl group, hexyl group or cyclohexyl group; alkenylazulenyl groups having one or more alkenyl group such as vinyl group or allyl group; arylazulenyl groups having one or more aryl group such as phenyl group, dimethylphenyl group, diethylphenyl group, dipropylphenyl group, dibutylphenyl group, trimethylphenyl group, triethylphenyl group, tripropylphenyl group, tributylphenyl group, biphenyl group, naphthyl group or anthryl group; and arylalkylazulenyl groups having one or more arylalkyl group such as trityl group, phenethyl group, styryl group, benzhydryl group, phenylpropyl group, phenylbutyl group and neophyl group. These substituents can be branched ones.

Structural Formula 1

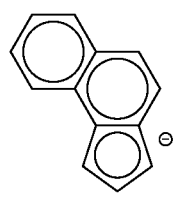

Structural Formula 2

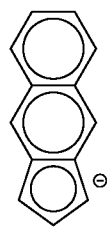

Structural Formula 3

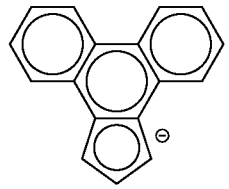

The above groups are exemplified more particularly by indenyl group, methylindenyl group, ethylindenyl group, propylindenyl group, butylindenyl group,. vinylindenyl group, allylindenyl group, phenylindenyl group, tolylindenyl group, biphenylindenyl group, naphthylindenyl group, anthryl-indenyl group, benzylindenyl group, dimethyindenyl group, trimethylindenyl group, tetramethylindenyl group, diethylindenyl group, triethylihdenyl group, tetraethylindenyl group, dipropylindenyl group, tripropylindenyl group, tetrapropylindenyl group, dibutylindenyl group, tributylindenyl group, tetrabutylindenyl group, diphenylindenyl group, methylphenylindenyl group, methylnaphthylindlenyl group, methylanthrylindenyl group, benzoindenyl group, methylbenzoindenyl group and dibenzoindenyl group.

Among them, preferable groups are exemplified by indenyl group, methylindenyl group, propylindenyl group, tetramethylindenyl group, tetraethylindenyl group, tetrapropylindenyl group, tetrabutylindenyl group, phenylindenyl group, naphthylindenyl group, biphenylindenyl group, benzo-indenyl group and dibenzoindenyl group. The indenyl group, tetramethyl-indenyl group, phenylindenyl group, benzoindenyl group and dibenzoindenyl group are more preferable.

The symbol $M^1$ denotes a transition metal of group 4 of the periodic table.

In the transition metal compounds of the present invention as-represented by the foregoing general formula (2), each of $(C_5R^{16}R^{17}R^{18}R^{19}R^{20})$, $(C_5R^{21}R^{22}R^{23}R^{24}R^{25})$ and $(C5H_2R^{26}R^{27}R^{28})$ denotes a cyclopentadienyl group or a substituted cyclopentadienyl group, in which the structures of $R^{16}$ to $R^{28}$ can be selected from similar structures of $R^1$ to $R^{15}$ as indicated in the description of the foregoing transition metal compounds of general formula (1). However, at least one of $R^{16}$ to $R^{28}$ must be a substituent group other than hydrogen atom. Furthermore, the symbol $M^2$ denotes a transition metal of group 4 of the periodic table.

In the transition metal compounds of the general formula (2) in the present invention, the substituent groups of $R^{26}$, $R^{27}$ and $R^{28}$ in the substituted cyclopentadienyl group of $(C_5R^{26}R^{27}R^{28})$ are preferably bonded to their adjacent carbon atoms of 1-position, 2-position and 3-position of the cyclopentadienyl group.

In the transition metal compounds of the general formula (3) in the present invention, $(C_5H_2R^{29}R^{30}R^{31})$, $(C_5H_2R^{32}R^{33}R^{34})$ and $(C_5H_2R^{35}R^{36}\ R^{37})$ denote cyclopentadienyl groups or substituted cyclopentadienyl groups, respectively. The substituent groups of $R^{29}$ to $R^{37}$ can be selected from similar structures of $R^1$ to $R^{15}$ in the description of the transition metal compounds of the general formula (1). However, at least one of $R^{29}$ to $R^{37}$ must be a substituent group other than hydrogen atom. The symbol $M^3$ denotes a transition metal of group 4 of the periodic table.

In the transition metal compound of the general formula (3), the substituent groups of $R^{29}$, $R^{30}$ and $R^{31}$; $R^{32}$, $R^{33}$ and $R^{34}$; or $R^{35}$, $R^{36}$ and $R^{37}$; of the cyclopentadienyl groups are preferably bonded to their adjacent carbon atom of 1-position, 2-position and 3-position of the cyclopentadienyl group. It is more preferable that the three substituted cyclopentadienyl groups of $(C_5H_2R^{29}R^{30}R^{31})$, $(C_5H_2R^{32}R^{33}R^{34})$ and $(C_5H_2R^{35}R^{36}R^{37})$, are of the same structure.

In the transition metal compounds of the general formula (4) of the present invention, $(C_5H_3R^{38}R^{39})$, $(C_5H_3R^{40}R^{41})$ and $(C_5H_3R^{42}R^{43})$ denote cyclopentadienyl groups or substituted cyclopentadienyl groups, respectively. $R^{38}$, $R^{39}$, $R^{40}$, $R^{41}$, $R^{42}$ and $R^{43}$ denote substituent groups of the cyclopentadienyl group or substituted cyclopentadienyl group. $R^{38}$ to $R^{43}$ can be selected from similar structures of $R^1$ to $R^{15}$ in the description of the foregoing transition metal compounds of the general formula (1). At least one of $R^{38}$ to $R^{43}$ must be a substituent other than hydrogen atom. The symbol $M^4$ denotes a transition metal of group 4 of the periodic table.

In the transition metal compounds of the general formula (4) of the present invention, it is preferable that the three substituted cyclopentadienyl groups of $(C_5H_3R^{38}R^{39})$, $(C_5H_3R^{40}R^{41})$ and $(C_5H_3R^{42}R^{43})$ are the same.

In the transition metal compound of the general formula (5) of the present invention, $(C_9R^{44}R^{45}R^{46}R^{47}R^{48}R^{49}R^{50})$, $(C_9R^{51}R^{52}R^{53}R^{54}R^{55}R^{56}R^{57})$ and $(C_9R^{58}R^{59}R^{60}R^{61}R^{62}R^{63}R^{64})$ denote indenyl groups or substituted indenyl groups, respectively. $R^{44}$ to $R^{64}$ are any one of hydrogen atom, a hydrocarbon group having 1 to 30 carbon atoms or an organosilicon group having a substituent of hydrocarbon having 1 to 30 carbon atoms, which may be the same or different from one another. However, the number of carbon atoms is preferably 1 to 24, and more preferably 1 to 18. The hydrocarbon groups of $R^{44}$ to $R^{64}$ are exemplified by alkyl groups such as methyl group, ethyl group, propyl group, butyl group, pentyl group, hexyl group or cyclohexyl group; alkenyl groups such as vinyl group or allyl group; aryl groups such as phenyl group, dimethylphenyl group, diethylphenyl group, dipropylphenyl group, dibutylphenyl group, trimethylphenyl group, triethylphenyl group, tripropyl-phenyl group, tributylphenyl group, biphenyl group, naphthyl group or anthryl group; and arylalkyl groups such as trityl group, phenethyl group, styryl group, benzhydryl group, phenylpropyl group, phenylbutyl group or neophyl group. These groups can be branched ones.

They are more particularly exemplified by methyl group, ethyl group, propyl group, butyl group, cyclohexyl group, vinyl group, allyl group and phenyl group. Above all, methyl group, ethyl group, propyl group, butyl group and phenyl group are more preferable.

The organosilicon groups having substituent of hydrocarbon with 1 to 30 carbon atoms of $R^{44}$ to $R^{64}$ are exemplified by alkylsilyl groups having substituent of alkyl group such as methyl group, ethyl group, propyl group, butyl group, pentyl group, hexyl group or cyclohexyl group; alkenylsilyl groups having substituent of alkenyl group such as vinyl group or allyl group; arylsilyl groups having substituent of aryl group such as phenyl group, dimethylphenyl group, diethylphenyl group, dipropylphenyl group, dibutyl-phenyl group, trimethylphenyl group, triethylphenyl group, tripropylphenyl group, tributylphenyl group, biphenyl group, naphthyl group or anthryl group; and arylalkylsilyl groups having substituent of arylalkyl group such as trityl group, phenethyl group, styryl group, benzhydryl group, phenylpropyl group, phenylbutyl group or neophyl group. These groups can be branched ones.

More particularly, they are exemplified by trimethylsilyl group, triethylsilyl group, tripropylsilyl group, tributylsilyl group, trivinylsilyl group, triallylsilyl group and triphenylsilyl group. Among them, trimethylsilyl group, triethylsilyl group and triphenylsilyl group are more preferable.

In the groups of $R^{44}$ to $R^{50}$ or $R^{51}$ to $R^{57}$ or $R^{58}$ to $R^{64}$, they can be bonded to one another forming a cyclic hydrocarbon group (including polycyclic structure).

The cyclic hydrocarbon groups (including polycyclic structure) that is formed through the bonding are exemplified by benzoindenyl group; alkylbenzoindenyl groups having one or more alkyl group such as methyl group, ethyl group, propyl group, butyl group, pentyl group, hexyl group or cyclohexyl group; alkenylbenzoindenyl groups having one or more alkenyl group such as vinyl group or allyl group; arylbenzoindenyl groups having one or more aryl group such as phenyl group, dimethylphenyl group, diethylphenyl group, dipropylphenyl group, dibutylphenyl group, trimethylphenyl group, triethylphenyl group, tripropylphenyl group, tributylphenyl group, biphenyl group, naphthyl group or anthryl group; arylalkylbenzoindenyl groups having one or more arylalkyl group such as trityl group, phenethyl group, styryl group, benzhydryl group, phenylpropyl group, phenylbutyl group or neophyl group; dibenzoindenyl group; alkyldibenzoindenyl groups having one or more alkyl group such as methyl group, ethyl group, propyl group, butyl group, pentyl group, hexyl group or cyclohexyl group; alkenyldibenzoindenyl groups having one or more alkenyl group such as vinyl group or allyl group; aryldibenzoindenyl groups having one or more aryl group such as phenyl group, dimethylphenyl group, diethylphenyl group, dipropylphenyl group, dibutylphenyl group, tri-methylphenyl group, triethylphenyl group, tripropylphenyl group, tributylphenyl group, biphenyl group, naphthyl group or anthryl group; and arylalkyldibenzoindenyl groups having one or more arylalkyl group such as trityl group, phenethyl group, styryl group, benzhydryl group, phenylpropyl group, phenylbutyl group or neophyl group. These groups can be branched ones.

More particularly, they are exemplified by benzoindenyl group, methylbenzoindenyl group, dimethylbenzoindenyl group, phenylbenzoindenyl group, diphenylbenzoindenyl group, dibenzoindenyl group, methyldibenzo-indenyl group and dimethyldibenzoindenyl group.

Among them, benzoindenyl group and dibenzoindenyl group are more preferable.

The symbol $M^5$ denotes a transition metal of group 4 of the periodic table.

In the transition metal compound of the general formula (6) of the present invention, the groups of $(C_9H_3R^{65}R^{66}R^{67}R^{68})$, $(C_9H_3R^{69}R^{70}R^{71}R^{72})$ and $(C_9H_3R^{73}R^{74}R^{75}R^{76})$ denote indenyl groups or substituted indenyl groups, respectively.. The $R^{65}$ to $R^{76}$ can be selected from similar structure ones as $R^{44}$ to $R^{64}$ that were described in the foregoing transition metal compounds of the general formula (5). The symbol $M^6$ denotes a transition metal of group 4 of the periodic table. The groups of $R^{65}$ to $R^{68}$; and $R^{69}$ to $R^{72}$; and $R^{73}$ to $R^{76}$ are bonded to carbon atoms of 4-position, 5-position, 6-position and 7-position (positions in the six-membered ring) of the respective indenyl group and they can be bonded to one another forming a cyclic hydrocarbon group (including polycyclic structure).

In the structure of the transition metal compound of the general formula (6), it is preferable that the three substituted indenyl groups of $(C_9H_3R^{65}R^{66}R^{67}R^{68})$, $(C_9H_3R^{69}R^{70}R^{71}R^{72})$ and $(C_9C_3R^{73}R^{74}R^{75}R^{76})$ are the same in structure.

As the transition metals of group 4 of the periodic table in the transition metal compounds, Ti, Zr and Hf are exemplified. Among them, Ti and Zr are preferable, and Zr is more preferable.

In the following, examples of the transition metal compounds of the present invention are indicated. While, the invention is not limited to these examples.

Cp$_2$(MeCp)ZrH,
Cp$_2$(PrCp)ZrH,
Cp$_2$(PhCp)ZrH,
Cp$_2$(MeEtCp)ZrH,
Cp$_2$(MeBuCp)ZrH,
Cp$_2$(Et$_2$Cp)ZrH,
Cp$_2$(Et$_3$SiCp)ZrH,
Cp$_2$((Me$_3$Si)$_2$Cp)ZrH,
Cp$_2$(Et$_3$Cp)ZrH,
Cp$_2$(Bu$_3$Cp)ZrH,
Cp$_2$(Et$_4$Cp)ZrH,
Cp$_2$(Bu$_4$Cp)ZrH,
(MeCp)$_2$(Cp)ZrH,
(MeCp)$_2$(PrCp)ZrH,
(MeCp)$_2$(PhCp)ZrH,
(MeCp)$_2$(MeEtCp)ZrH,
(MeCp)$_2$(MeBuCp)ZrH,
(MeCp)$_2$(Et$_2$Cp)ZrH,
(MeCp)$_2$(Et$_3$SiCp)ZrH,
(MeCp)$_2$((Me$_3$Si)$_2$Cp)ZrH,
(MeCp)$_2$(Et$_3$Cp)ZrH,
(MeCp)$_2$(Bu$_3$Cp)ZrH,
(MeCp)$_2$(Et$_4$Cp)ZrH,
(MeCp)$_2$(Bu$_4$Cp)ZrH,
(BuCp)$_2$(Cp)ZrH,
(BuCp)$_2$(EtCp)ZrH,
(BuCp)$_2$(PhCp)ZrH,
(BuCp)$_2$(MeEtCp)ZrH,
(BuCp)$_2$(MeBuCp)ZrH,
(BuCp)$_2$(Et$_2$Cp)ZrH,
(BuCp)$_2$(Et$_3$SiCp)ZrH,
(BuCp)$_2$((Me$_3$Si)$_2$Cp)ZrH,
(BuCp)$_2$(Et$_3$Cp)ZrH,
(BuCp)$_2$(Bu$_3$Cp)ZrH,
(BuCp)$_2$(Et$_4$Cp)ZrH,
(BuCp)$_2$(Bu$_4$Cp)ZrH,
(Me$_3$SiCp)$_2$(Cp)ZrH,
(Me$_3$SiCp)$_2$(EtCp)ZrH,
(Me$_3$SiCp)$_2$(BuCp)ZrH,
(Me$_3$SiCp)$_2$(Me$_2$Cp)ZrH,
(Me$_3$SiCp)$_2$(MePrCp)ZrH,
(Me$_3$SiCp)$_2$(MePhCp)ZrH,
(Me$_3$SiCp)$_2$(Et$_3$SiCp)ZrH,
(Me$_3$SiCp)$_2$((Me$_3$Si)$_2$Cp)ZrH,
(Me$_3$SiCp)$_2$(Et$_3$Cp)ZrH,
(Me$_3$SiCp)$_2$(Bu$_3$Cp)ZrH,
(Me$_3$SiCp)$_2$(Et$_4$Cp)ZrH,
(Me$_3$SiCp)$_2$(Bu$_4$Cp)ZrH,
(Me$_2$Cp)$_2$(Cp)ZrH,
(Me$_2$Cp)$_2$(EtCp)ZrH,
(Me$_2$Cp)$_2$(BuCp)ZrH,
(Me$_2$Cp)$_2$(MeEtCp)ZrH,
(Me$_2$Cp)$_2$(MeBuCp)ZrH,
(Me$_2$Cp)$_2$(Et$_2$Cp)ZrH,
(Me$_2$Cp)$_2$(Ph$_3$SiCp)ZrH,
(Me$_2$Cp)$_2$(Me$_3$Cp)ZrH,
(Me$_2$Cp)$_2$(Pr$_3$Cp)ZrH,
(Me$_2$Cp)$_2$(Me$_4$Cp)ZrH,
(Me$_2$Cp)$_2$(Pr$_4$Cp)ZrH,
(Me$_2$Cp)$_2$(Me$_5$Cp)ZrH,
(Me$_3$Cp)$_2$(MeCp)ZrH,
(Me$_3$Cp)$_2$(PrCp)ZrH,
(Me$_3$Cp)$_2$(PhCp)ZrH,
(Me$_3$Cp)$_2$(MeEtCp)ZrH,
(Me$_3$Cp)$_2$(MeBuCp)ZrH,
(Me$_3$Cp)$_2$(Et$_2$Cp)ZrH,
(Me$_3$Cp)$_2$(Ph$_3$SiCp)ZrH,
(Me$_3$Cp)$_2$(Et$_3$SiCp)ZrH,
(Me$_3$Cp)$_2$(Bu$_3$Cp)ZrH,
(Me$_3$Cp)$_2$(Et$_4$Cp)ZrH,
Cp$_2$(EtCp)ZrH,
Cp$_2$(BuCp)ZrH,
Cp$_2$(Me$_2$Cp)ZrH,
Cp$_2$(MePrCp)ZrH,
Cp$_2$(MePhCp)ZrH,
Cp$_2$(Me$_3$SiCp)ZrH,
Cp$_2$(Ph$_3$SiCp)ZrH,
Cp$_2$(Me$_3$Cp)ZrH,
Cp$_2$(Pr$_3$Cp)ZrH,
Cp$_2$(Me$_4$Cp)ZrH,
Cp$_2$(Pr$_4$Cp)ZrH,
Cp$_2$(Me$_5$Cp)ZrH,
(MeCp)$_2$(EtCp)ZrH,
(MeCp)$_2$(BuCp)ZrH,
(MeCp)$_2$(Me$_2$Cp)ZrH,
(MeCp)$_2$(MePrCp)ZrH,
(MeCp)$_2$(MePhCp)ZrH,
(MeCp)$_2$(Me$_3$SiCp)ZrH,
(MeCp)$_2$(Ph$_3$SiCp)ZrH,
(MeCp)$_2$(Me$_3$Cp)ZrH,
(MeCp)$_2$(Pr$_3$Cp)ZrH,
(MeCp)$_2$(Me$_4$Cp)ZrH,
(MeCp)$_2$(Pr$_4$Cp)ZrH,
(MeCp)$_2$(Me$_5$Cp)ZrH,
(BuCp)$_2$(MeCp)ZrH,
(BuCp)$_2$(PrCp)ZrH,
(BuCp)$_2$(Me$_2$Cp)ZrH,
(BuCp)$_2$(MePrCp)ZrH,
(BuCp)$_2$(MePhCp)ZrH,
(BuCp)$_2$(Me$_3$SiCp)ZrH,
(BuCp)$_2$(Ph$_3$SiCp)ZrH,
(BuCp)$_2$(Me$_3$Cp)ZrH,
(BuCp)$_2$(Pr$_3$Cp)ZrH,
(BuCp)$_2$(Me$_4$Cp)ZrH,
(BuCp)$_2$(Pr$_4$Cp)ZrH,
(BuCp)$_2$(Me$_5$Cp)ZrH,
(Me$_3$SiCp)$_2$(MeCp)ZrH,
(Me$_3$SiCp)$_2$(PrCp)ZrH,
(Me$_3$SiCp)$_2$(PhCp)ZrH,
(Me$_3$SiCp)$_2$(MeEtCp)ZrH,
(Me$_3$SiCp)$_2$(MeBuCp)ZrH,
(Me$_3$SiCp)$_2$(Et$_2$Cp)ZrH,
Me$_3$SiCp)$_2$(Ph$_3$SiCp)ZrH,
(Me$_3$SiCp)$_2$(Me$_3$Cp)ZrH,
(Me$_3$SiCp)$_2$(Pr$_3$Cp)ZrH,
(Me$_3$SiCp)$_2$(Me$_4$Cp)ZrH,
(Me$_3$SiCp)$_2$(Pr$_4$Cp)ZrH,
(Me$_3$SiCp)$_2$(Me$_5$Cp)ZrH,
(Me$_2$Cp)$_2$(MeCp)ZrH,
(Me$_2$Cp)$_2$(PrCp)ZrH,
(Me$_2$Cp)$_2$(PhCp)ZrH,
(Me$_2$Cp)$_2$(MePrCp)ZrH,
(Me$_2$Cp)$_2$(MePhCp)ZrH,
(Me$_2$Cp)$_2$(Et$_3$SiCp)ZrH,
(Me$_2$Cp)$_2$((Me$_3$Si)$_2$Cp)ZrH,
(Me$_2$Cp)$_2$(Et$_3$Cp)ZrH,
(Me$_2$Cp)$_2$(Bu$_3$Cp)ZrH,
(Me$_2$Cp)$_2$(Et$_4$Cp)ZrH,
(Me$_2$Cp)$_2$(Bu$_4$Cp)ZrH,
(Me$_3$Cp)$_2$(Cp)ZrH,
(Me$_3$Cp)$_2$(EtCp)ZrH,
(Me$_3$Cp)$_2$(BuCp)ZrH,
(Me$_3$Cp)$_2$(Me$_2$Cp)ZrH,
(Me$_3$Cp)$_2$(MePrCp)ZrH,
(Me$_3$Cp)$_2$(MePhCp)ZrH,
(Me$_3$Cp)$_2$(Et$_3$SiCp)ZrH,
MesCp)$_2$((Me$_3$Si)$_2$Cp)ZrH,
(Me$_3$Cp)$_2$(Pr$_3$Cp)ZrH,
(Me$_3$Cp)$_2$(Me$_4$Cp)ZrH,
(Me$_3$Cp)$_2$(Pr$_4$Cp)ZrH,

-continued (Me$_3$Cp)$_2$(Bu$_4$Cp)ZrH,
(MeCp)$_3$ZrH,
(PrCp)$_3$ZrH,
(PhCp)$_3$ZrH,
(Et$_3$SiCp)$_3$ZrH,
(Me$_2$Cp)$_3$ZrH,
(Pr$_2$Cp)$_3$ZrH,
(Me$_3$Cp)$_3$ZrH,
(Pr$_3$Cp)$_3$ZrH,
(Me$_4$Cp)$_3$ZrH,
(Pr$_4$Cp)$_3$ZrH,
(Me$_5$Cp)$_3$ZrH,
(Pr$_5$Cp)$_3$ZrH,
Ind$_2$(Cp)ZrH,
Ind$_2$(EtCp)ZrH,
Ind$_2$(BuCp)ZrH,
Ind$_2$(Me$_2$Cp)ZrH,
Ind$_2$(MePrCp)ZrH,
Ind$_2$(MePhCp)ZrH,
Ind$_2$(Me$_3$SiCp)ZrH,
Ind$_2$(Ph$_3$SiCp)ZrH,
Ind$_2$(Me$_3$Cp)ZrH,
Ind$_2$(Pr$_3$Cp)ZrH,
Ind$_2$(Me$_4$Cp)ZrH,
Ind$_2$(Pr$_4$Cp)ZrH,
Ind$_2$(Me$_5$Cp)ZrH,
(Cp)(Ind)(EtCp)ZrH,
(Cp)(Ind)(BuCp)ZrH,
(Cp)(Ind)(Me$_2$Cp)ZrH,
(Cp)(Ind)(MePrCp)ZrH,
(Cp)(Ind)(MePhCp)ZrH,
(Cp)(Ind)(Me$_3$SiCp)ZrH,
(Cp)(Ind)(Ph$_3$SiCp)ZrH,
(Cp)(Ind)(Me$_3$Cp)ZrH,
(Cp)(Ind)(Pr$_3$Cp)ZrH,
(Cp)(Ind)(Me$_4$Cp)ZrH,
(Cp)(Ind)(Pr$_4$Cp)ZrH,
(Cp)(Ind)(Me$_5$Cp)ZrH,
MeInd$_2$(MeCp)ZrH,
MeInd$_2$(PrCp)ZrH,
MeInd$_2$(PhCp)ZrH,
MeInd$_2$(MeEtCp)ZrH,
MeInd$_2$(MeBuCp)ZrH,
MeInd$_2$(Et$_2$Cp)ZrH,
MeInd$_2$(Et$_3$SiCp)ZrH,
MeInd$_2$((Me$_3$Si)$_2$Cp)ZrH,
MeInd$_2$(Et$_3$Cp)ZrH,
MeInd$_2$(Bu$_3$Cp)ZrH,
MeInd$_2$(Et$_4$Cp)ZrH,
MeInd$_2$(Bu$_4$Cp)ZrH,
(Cp)(MeInd)(MeCp)ZrH,
(Cp)(MeInd)(PrCp)ZrH,
(Cp)(MeInd)(PhCp)ZrH,
(Cp)(MeInd)(MeEtCp)ZrH,
(Cp)(MeInd)(MeBuCp)ZrH,
(Cp)(MeInd)(Et$_2$Cp)ZrH,
(Cp)(MeInd)(Et$_3$SiCp)ZrH,
(Cp)(MeInd)((Me$_3$Si)$_2$Cp)ZrH,
(Cp)(MeInd)(Et$_3$Cp)ZrH,
(Cp)(MeInd)(Bu$_3$Cp)ZrH,
(Cp)(MeInd)(Et$_4$Cp)ZrH,
(Cp)(MeInd)(Bu$_4$Cp)ZrH,
PhInd$_2$(Cp)ZrH,
PhInd$_2$(EtCp)ZrH,
PhInd$_2$(BuCp)ZrH,
PhInd$_2$(Me$_2$Cp)ZrH,
PhInd$_2$(MePrCp)ZrH,
PhInd$_2$(MePhCp)ZrH,
PhInd$_2$(Me$_3$SiCp)ZrH,
PhInd$_2$(Ph$_3$SiCp)ZrH,
PhInd$_2$(Me$_3$Cp)ZrH,
PhInd$_2$(Pr$_3$Cp)ZrH,
PhInd$_2$(Me$_4$Cp)ZrH,
PhInd$_2$(Pr$_4$Cp)ZrH,
PhInd$_2$(Me$_5$Cp)ZrH,
(Cp)(PhInd)(EtCp)ZrH,
(Cp)(PhInd)(BuCp)ZrH,
(Cp)(PhInd)(Me$_2$Cp)ZrH,
(Cp)(PhInd)(MePrCp)ZrH,
(Me$_3$Cp)$_2$(Me$_5$Cp)ZrH,
(EtCp)$_3$ZrH,
(BuCp)$_3$ZrH,
(Me$_3$SiCp)$_3$ZrH,
(Ph$_3$SiCp)$_3$ZrH,
(Et$_2$Cp)$_3$ZrH,.
(Bu$_2$Cp)$_3$ZrH,
(Et$_3$Cp)$_3$ZrH,
(Bu$_3$Cp)$_3$ZrH,
(Et$_4$Cp)$_3$ZrH,
(Bu$_4$Cp)$_3$ZrH,
(Et$_5$Cp)$_3$ZrH,
(Bu$_5$Cp)$_3$ZrH,
Ind$_2$(MeCp)ZrH,
Ind$_2$(PrCp)ZrH,
Ind$_2$(PhCp)ZrH,
Ind$_2$(MeEtCp)ZrH,
Ind$_2$(MeBuCp)ZrH,
Ind$_2$(Et$_2$Cp)ZrH,
Ind$_2$(Et$_3$SiCp)ZrH,
Ind$_2$((Me$_3$Si)$_2$Cp)ZrH,
Ind$_2$(Et$_3$Cp)ZrH,
Ind$_2$(Bu$_3$Cp)ZrH,
Ind$_2$(Et$_4$Cp)ZrH,
Ind$_2$(Bu$_4$Cp)ZrH,
(Cp)(Ind)(MeCp)ZrH,
(Cp)(Ind)(PrCp)ZrH,
(Cp)(Ind)(PhCp)ZrH,
(Cp)(Ind)(MeEtCp)ZrH,
(Cp)(Ind)(MeBuCp)ZrH,
(Cp)(Ind)(Et$_2$Cp)ZrH,
(Cp)(Ind)(Et$_3$SiCp)ZrH,
(Cp)(Ind)((Me$_3$Si)$_2$Cp)ZrH,
(Cp)(Ind)(Et$_3$Cp)ZrH,
(Cp)(Ind)(Bu$_3$Cp)ZrH,
(Cp)(Ind)(Et$_4$Cp)ZrH,
(Cp)(Ind)(Bu$_4$Cp)ZrH,
MeInd$_2$(Cp)ZrH,
MeInd$_2$(EtCp)ZrH,
MeInd$_2$(BuCp)ZrH,
MeInd$_2$(Me$_2$Cp)ZrH,
MeInd$_2$(MePrCp)ZrH,
MeInd$_2$(MePhCp)ZrH,
MeInd$_2$(Me$_3$SiCp)ZrH,
MeInd$_2$(Ph$_3$SiCp)ZrH,
MeInd$_2$(Me$_3$Cp)ZrH,
MeInd$_2$(Pr$_3$Cp)ZrH,
MeInd$_2$(Me$_4$Cp)ZrH,
MeInd$_2$(Pr$_4$Cp)ZrH,
MeInd$_2$(Me$_5$Cp)ZrH,
(Cp)(MeInd)(EtCp)ZrH,
(Cp)(MeInd)(BuCp)ZrH,
(Cp)(MeInd)(Me$_2$Cp)ZrH,
(Cp)(MeInd)(MePrCp)ZrH,
(Cp)(MeInd)(MePhCp)ZrH,
(Cp)(MeInd)(Me$_3$SiCp)ZrH,
(Cp)(MeInd)(Ph$_3$SiCp)ZrH,
(Cp)(MeInd)(Me$_3$Cp)ZrH,
(Cp)(MeInd)(Pr$_3$Cp)ZrH,
(Cp)(MeInd)(Me$_4$Cp)ZrH,
(Cp)(MeInd)(Pr$_4$Cp)ZrH,
(Cp)(MeInd)(Me$_5$Cp)ZrH,
PhInd$_2$(MeCp)ZrH,
PhInd$_2$(PrCp)ZrH,
PhInd$_2$(PhCp)ZrH,
PhInd$_2$(MeEtCp)ZrH,
PhInd$_2$(MeBuCp)ZrH,
PhInd$_2$(Et$_2$Cp)ZrH,
PhInd$_2$(Et$_3$SiCp)ZrH,
PhInd$_2$((Me$_3$Si)$_2$Cp)ZrH,
PhInd$_2$(Et$_3$Cp)ZrH,
PhInd$_2$(Bu$_3$Cp)ZrH,
PhInd$_2$(Et$_4$Cp)ZrH,
PhInd$_2$(Bu$_4$Cp)ZrH,
(Cp)(PhInd)(MeCp)ZrH,
(Cp)(PhInd)(PrCp)ZrH,
(Cp)(PhInd)(PhCp)ZrH,
(Cp)(PhInd)(MeEtCp)ZrH,
(Cp)(PhInd)(MeBuCp)ZrH, -continued (Cp)(PhInd)(MePhCp)ZrH,
(Cp)(PhInd)(Me$_3$SiCp)ZrH,
(Cp)(PhInd)(Ph$_3$SiCp)ZrH,
(Cp)(PhInd)(Me$_3$Cp)ZrH,
(Cp)(PhInd)(Pr$_3$Cp)ZrH,
(Cp)(PhInd)(Me$_4$Cp)ZrH,
(Cp)(PhInd)(Pr$_4$Cp)ZrH,
(Cp)(PhInd)(Me$_5$Cp)ZrH,
Me$_4$Ind$_2$(MeCp)ZrH,
Me$_4$Ind$_2$(PrCp)ZrH,
Me$_4$Ind$_2$(PhCp)ZrH,
Me$_4$Ind$_2$(MeEtCp)ZrH,
Me$_4$Ind$_2$(MeBuCp)ZrH,
Me$_4$Ind$_2$(Et$_2$Cp)ZrH,
Me$_4$Ind$_2$(Et$_3$SiCp)ZrH,
Me$_4$Ind$_2$((Me$_3$Si)$_2$Cp)ZrH,
Me$_4$Ind$_2$(Et$_3$Cp)ZrH,
Me$_4$Ind$_2$(Bu$_3$Cp)ZrH,
Me$_4$Ind$_2$(Et$_4$Cp)ZrH,
Me$_4$Ind$_2$(Bu$_4$Cp)ZrH,
(Cp)(Me$_4$Ind)(MeCp)ZrH,
(Cp)(Me$_4$Ind)(PrCp)ZrH,
(Cp)(Me$_4$Ind)(PhCp)ZrH,
(Cp)(Me$_4$Ind)(MeEtCp)ZrH,
(Cp)(Me$_4$Ind)(MeBuCp)ZrH,
(Cp)(Me$_4$Ind)(Et$_2$Cp)ZrH,
(Cp)(Me$_4$Ind)(Et$_3$SiCp)ZrH,
(Cp)(Me$_4$Ind)((Me$_3$Si)$_2$Cp)ZrH,
(Cp)(Me$_4$Ind)(Et$_3$Cp)ZrH,
(Cp)(Me$_4$Ind)(Bu$_3$Cp)ZrH,
(Cp)(Me$_4$Ind)(Et$_4$Cp)ZrH,
(Cp)(Me$_4$Ind)(Bu$_4$Cp)ZrH,
BenzInd$_2$(Cp)ZrH,
BenzInd$_2$(EtCp)ZrH,
BenzInd$_2$(BuCp)ZrH,
BenzInd$_2$(Me$_2$Cp)ZrH,
BenzInd$_2$(MePrCp)ZrH,
BenzInd$_2$(MePhCp)ZrH,
BenzInd$_2$(Me$_3$SiCp)ZrH,
BenzInd$_2$(Ph$_3$SiCp)ZrH,
BenzInd$_2$(Me$_3$Cp)ZrH,
BenzInd$_2$(Pr$_3$Cp)ZrH,
BenzInd$_2$(Me$_4$Cp)ZrH,
BenzInd$_2$(Pr$_4$Cp)ZrH,
BenzInd$_2$(Me$_5$Cp)ZrH,
(Cp)(BenzInd)(EtCp)ZrH,
(Cp)(BenzInd)(BuCp)ZrH,
(Cp)(BenzInd)(Me$_2$Cp)ZrH,
(Cp)(BenzInd)(MePrCp)ZrH,
(Cp)(BenzInd)(MePhCp)ZrH,
(Cp)(BenzInd)(Me$_3$SiCp)ZrH,
(Cp)(BenzInd)(Ph$_3$SiCp)ZrH,
(Cp)(BenzInd)(Me$_3$Cp)ZrH,
(Cp)(BenzInd)(Pr$_3$Cp)ZrH,
(Cp)(BenzInd)(Me$_4$Cp)ZrH,
(Cp)(BenzInd)(Pr$_4$Cp)ZrH,
(Cp)(BenzInd)(Me$_5$Cp)ZrH,
DibenzoInd$_2$(MeCp)ZrH,
DibenzoInd$_2$(PrCp)ZrH,
DibenzoInd$_2$(PhCp)ZrH,
DibenzoInd$_2$(MeEtCp)ZrH,
DibenzoInd$_2$(MeBuCp)ZrH,
DibenzoInd$_2$(Et$_2$Cp)ZrH,
DibenzoInd$_2$(Et$_3$SiCp)ZrH,
DibenzoInd$_2$((Me$_3$Si)$_2$Cp)ZrH,
DibenzoInd$_2$(Et$_3$Cp)ZrH,
DibenzoInd$_2$(Bu$_3$Cp)ZrH,
DibenzoInd$_2$(Et$_4$Cp)ZrH,
DibenzoInd$_2$(Bu$_4$Cp)ZrH,
(Cp)(DibenzoInd)(MeCp)ZrH,
(Cp)(DibenzoInd)(PrCp)ZrH,
(Cp)(DibenzoInd)(PhCp)ZrH,
(Cp)(DibenzoInd)(MeEtCp)ZrH,
(Cp)(DibenzoInd)(MeBuCp)ZrH,
(Cp)(DibenzoInd)(Et$_2$Cp)ZrH,
(Cp)(DibenzoInd)(Et$_3$SiCp)ZrH,
(Cp)(DibenzoInd)((Me$_3$Si)$_2$Cp)ZrH,
(Cp)(DibenzoInd)(Et$_3$Cp)ZrH,
(Cp)(DibenzoInd)(Bu$_3$Cp)ZrH,
(Cp)(PhInd)(Et$_2$Cp)ZrH,
(Cp)(PhInd)(Et$_3$SiCp)ZrH,
(Cp)(PhInd)((Me$_3$Si)$_2$Cp)ZrH,
(Cp)(PhInd)(Et$_3$Cp)ZrH,
(Cp)(PhInd)(Bu$_3$Cp)ZrH,
(Cp)(PhInd)(Et$_4$Cp)ZrH,
(Cp)(PhInd)(Bu$_4$Cp)ZrH,
Me$_4$Ind$_2$(Cp)ZrH,
Me$_4$Ind$_2$(EtCp)ZrH,
Me$_4$Ind$_2$(BuCp)ZrH,
Me$_4$Ind$_2$(Me$_2$Cp)ZrH,
Me$_4$Ind$_2$(MePrCp)ZrH,
Me$_4$Ind$_2$(MePhCp)ZrH,
Me$_4$Ind$_2$(Me$_3$SiCp)ZrH,
Me$_4$Ind$_2$(Ph$_3$SiCp)ZrH,
Me$_4$Ind$_2$(Me$_3$Cp)ZrH,
Me$_4$Ind$_2$(Pr$_3$Cp)ZrH,
Me$_4$Ind$_2$(Me$_4$Cp)ZrH,
Me$_4$Ind$_2$(Pr$_4$Cp)ZrH,
Me$_4$Ind$_2$(Me$_5$Cp)ZrH,
(Cp)(Me$_4$Ind)(EtCp)ZrH,
(Cp)(Me$_4$Ind)(BuCp)ZrH,
(Cp)(Me$_4$Ind)(Me$_2$Cp)ZrH,
(Cp)(Me$_4$Ind)(MePrCp)ZrH,
(Cp)(Me$_4$Ind)(MePhCp)ZrH,
(Cp)(Me$_4$Ind)(Me$_3$SiCp)ZrH,
(Cp)(Me$_4$Ind)(Ph$_3$SiCp)ZrH,
(Cp)(Me$_4$Ind)(Me$_3$Cp)ZrH,
(Cp)(Me$_4$Ind)(Pr$_3$Cp)ZrH,
(Cp)(Me$_4$Ind)(Me$_4$Cp)ZrH,
(Cp)(Me$_4$Ind)(Pr$_4$Cp)ZrH,
(Cp)(Me$_4$Ind)(Me$_5$Cp)ZrH,
BenzInd$_2$(MeCp)ZrH,
BenzInd$_2$(PrCp)ZrH,
BenzInd$_2$(PhCp)ZrH,
BenzInd$_2$(MeEtCp)ZrH,
BenzInd$_2$(MeBuCp)ZrH,
BenzInd$_2$(Et$_2$Cp)ZrH,
BenzInd$_2$(Et$_3$SiCp)ZrH,
BenzInd$_2$((Me$_3$Si)$_2$Cp)ZrH,
BenzInd$_2$(Et$_3$Cp)ZrH,
BenzInd$_2$(Bu$_3$Cp)ZrH,
BenzInd$_2$(Et$_4$Cp)ZrH,
BenzInd$_2$(Bu$_4$Cp)ZrH,
(Cp)(BenzInd)(MeCp)ZrH,
(Cp)(BenzInd)(PrCp)ZrH,
(Cp)(BenzInd)(PhCp)ZrH,
(Cp)(BenzInd)(MeEtCp)ZrH,
(Cp)(BenzInd)(MeBuCp)ZrH,
(Cp)(BenzInd)(Et$_2$Cp)ZrH,
(Cp)(BenzInd)(Et$_3$SiCp)ZrH,
(Cp)(BenzInd)((Me$_3$Si)$_2$Cp)ZrH,
(Cp)(BenzInd)(Et$_3$Cp)ZrH,
(Cp)(BenzInd)(Bu$_3$Cp)ZrH,
(Cp)(BenzInd)(Et$_4$Cp)ZrH,
(Cp)(BenzInd)(Bu$_4$Cp)ZrH,
DibenzoInd$_2$(Cp)ZrH,
DibenzoInd$_2$(EtCp)ZrH,
DibenzoInd$_2$(BuCp)ZrH,
DibenzoInd$_2$(Me$_2$Cp)ZrH,
DibenzoInd$_2$(MePrCp)ZrH,
DibenzoInd$_2$(MePhCp)ZrH,
DibenzoInd$_2$(Me$_3$SiCp)ZrH,
DibenzoInd$_2$(Ph$_3$SiCp)ZrH,
DibenzoInd$_2$(Me$_3$Cp)ZrH,
DibenzoInd$_2$(Pr$_3$Cp)ZrH,
DibenzoInd$_2$(Me$_4$Cp)ZrH,
DibenzoInd$_2$(Pr$_4$Cp)ZrH,
DibenzoInd$_2$(Me$_5$Cp)ZrH,
(Cp)(DibenzoInd)(EtCp)ZrH,
(Cp)(DibenzoInd)(BuCp)ZrH,
(Cp)(DibenzoInd)(Me$_2$Cp)ZrH,
(Cp)(DibenzoInd)(MePrCp)ZrH,
(Cp)(DibenzoInd)(MePhCp)ZrH,
(Cp)(DibenzoInd)(Me$_3$SiCp)ZrH,
(Cp)(DibenzoInd)(Ph$_3$SiCp)ZrH,
(Cp)(DibenzoInd)(Me$_3$Cp)ZrH,
(Cp)(DibenzoInd)(Pr$_3$Cp)ZrH,
(Cp)(DibenzoInd)(Me$_4$Cp)ZrH, -continued (Cp)(DibenzoInd)(Et$_4$Cp)ZrH,
(Cp)(DibenzoInd)(Bu$_4$Cp)ZrH,
Ind$_3$ZrH,
Ind$_2$(EtInd)ZrH,
Ind$_2$(BuInd)ZrH,
Ind$_2$(Me$_2$Ind)ZrH,
Ind$_2$(Pr$_2$Ind)ZrH,
Ind$_2$(Me$_4$Ind)ZrH,
Ind$_2$(Pr$_4$Ind)ZrH,
Ind$_2$(NaphInd)ZrH,
(MeInd)$_3$ZrH,
(PrInd)$_3$ZrH,
(Me$_3$SiInd)$_3$ZrH,
(NaphInd)$_3$ZrH,
(Me$_2$Ind)$_3$ZrH,
(Pr$_2$Ind)$_3$ZrH,
(Me$_2$Ind)$_2$(Ind)ZrH,
(Pr$_2$Ind)(Ind)ZrH,
(Ph$_2$Ind)$_2$(Ind)ZrH,
(Et$_3$Ind)$_3$ZrH,
(Bu$_3$Ind)$_3$ZrH,
(Et$_4$Ind)$_3$ZrH,
(Bu$_4$Ind)$_3$ZrH,
(BenzInd)$_2$(Ind)ZrH,
(DibenzoInd)$_2$(Ind)ZrH,
(DibenzoInd)$_3$ZrH,
(BenzInd)(DibenzoInd)$_2$ZrH, and
(Cp)(DibenzoInd)(Pr$_4$Cp)ZrH,
(Cp)(BenzInd)(Me$_5$Cp)ZrH,
Ind$_2$(MeInd)ZrH,
Ind$_2$(PrInd)ZrH,
Ind$_2$(Me$_3$SiInd)ZrH,
Ind$_2$(Et$_2$Ind)ZrH,
Ind$_2$(Bu$_2$Ind)ZrH,
Ind$_2$(Et$_4$Ind)ZrH,
Ind$_2$(Bu$_4$Ind)ZrH,
Ind$_2$(BiPhInd)ZrH,
(EtInd)$_3$ZrH,
(BuInd)$_3$ZrH,
(PhInd)$_3$ZrH,
(BiPhInd)$_3$ZrH,
(Et$_2$Ind)$_3$ZrH,
(Bu$_2$Ind)$_3$ZrH,
(Et$_2$Ind)$_2$(Ind)ZrH,
(Bu$_2$Ind)$_2$(Ind)ZrH,
(Me$_3$Ind)$_3$ZrH,
(Pr$_3$Ind)$_3$ZrH,
(Me$_4$Ind)$_3$ZrH,
(Pr$_4$Ind)$_3$ZrH,
(BenzInd)$_3$ZrH,
(BenzInd)(Ind)$_2$ZrH,
(DibenzoInd)(Ind)$_2$ZrH,
(BenzInd)$_2$(DibenzoInd)ZrH,
(DibenzoInd)(BenzInd)(Ind)ZrH.

In the above list of compounds, the following abbreviations were used for the respective groups (the same is applied to the description hereinafter). That is, Cp=cyclopentadienyl group, MeCp=methylcyclopentadienyl group, EtCp=ethylcyclopentadienyl group, PrCp=propylcyclopentadienyl group, BuCp=butylcyclopentadienyl group, PhCp=phenylcyclopentadienyl group, Me$_2$Cp=dimethylcyclopentadienyl group, MeEtCp=methylethylcyclopentadienyl group, MePrCp=methylpropylcyclopentadienyl group, MeBuCp=methylbutylcyclopentadienyl group, MePhCp=methylphenylcyclopentadienyl group, Et$_2$Cp=diethylcyclopentadienyl group, Me$_3$SiCp=trimethylsilylcyclopentadienyl group, Et$_3$SiCp=triethylsilylcyclopentadienyl group, Ph$_3$SiCp=triphenylsilylcyclopentadienyl group, (Me$_3$Si)$_2$Cp=bistrimethylsilylcyclopentadienyl group, Me$_3$Cp=trimethylcyclopentadienyl group, Et$_3$Cp=triethylcyclopentadienyl group, Pr$_3$Cp=tripropylcyclopentadienyl group, Bu$_3$Cp=tributylcyclopentadienyl group, Me$_4$Cp=tetramethylcyclopentadienyl group, Et$_4$Cp=tetraethylcyclopentadienyl group, Pr$_4$Cp=tetrapropylcyclopentadienyl group, Bu$_4$Cp=tetrabutylcyclopentadienyl group, Me$_5$Cp=pentamethylcyclopentadienyl group, Ind=indenyl group, MeInd=methylindenyl group, EtInd=ethylindenyl group, PrInd=propylindenyl group, BuInd=butylindenyl group, Me$_3$SiInd=trimethylsilylindenyl group, PhInd=phenylindenyl group, NaphInd=naphthylindenyl group, BiPhInd=biphenylindenyl group, Me$_2$Ind=dimethylindenyl group, Et$_2$Ind=diethylindenyl group, Pr$_2$Ind=dipropylindenyl group, Bu$_2$Ind=dibutylindenyl group, Me$_3$Ind=trimethylindenyl group, Et$_3$Ind=triethylindenyl group, Pr$_3$Ind=tripropylindenyl group, Bu$_3$Ind=tributylindenyl group, Me$_4$Ind=tetramethylindenyl group, Et$_4$Ind=tetraethylindenyl group, Pr$_4$Ind=tetrapropylindenyl group, Bu$_4$Ind=tetrabutylindenyl group, BenzInd=benzoindenyl group, and DiBenzoInd=dibenzoindenyl group.

It is also possible to use two or more of these compounds as the components of catalyst for olefin polymerization.

Among them, preferable compounds as the components of catalyst for olefin polymerization are exemplified by: $Cp_2(MeCp)ZrH$, $Cp_2(PrCp)ZrH$, $Cp_2(BuCp)ZrH$, $Cp_2(Me_2Cp)ZrH$, $Cp_2(MePrCp)ZrH$, $Cp_2(MeBuCp)ZrH$, $Cp_2(Me_3SiCp)ZrH$, $Cp_2(Me_3Cp)ZrH$, $(MeCp)_2(Cp)ZrH$, $(MeCp)_2(PrCp)ZrH$, $(MeCp)_2(BuCp)ZrH$, $(MeCp)_2(Me_2Cp)ZrH$, $(MeCp)_2(MePrCp)ZrH$, $(MeCp)_2(MeBuCp)ZrH$, $(MeCp)_2(Me_3SiCp)ZrH$, $(MeCp)_2(Me_3Cp)ZrH$, $(BuCp)_2(Cp)ZrH$, $(BuCp)_2(MeCp)ZrH$, $(BuCp)_2(PrCp)ZrH$, $(BuCp)_2(Me_2Cp)ZrH$, $(BuCP)_2(MePrCp)ZrH$, $(BuCp)_2(MeBuCp)ZrH$, $(BuCp)_2(Me_3SiCp)ZrH$, $(Me_3SiCp)_2(Cp)ZrH$, $(Me_3SiCp)_2(MeCp)ZrH$, $(Me_3SiCp)_2(PrCp)ZrH$, $(Me_3SiCp)_2(BuCp)ZrH$, $(Me_3SiCp)_2(Me_2Cp)ZrH$, $(Me_3SiCp)_2(MePrCp)ZrH$, $(Me_3SiCp)_2(MeBuCp)ZrH$, $(Me_3SiCp)_2(Me_3Cp)ZrH$, $(Me_2Cp)_2(Cp)ZrH$, $(Me_2Cp)2(MeCp)ZrH$, $(Me_2Cp)_2(PrCp)ZrH$, $(Me_2Cp)_2(BuCp)ZrH$, $(Me_2Cp)_2(MePrCp)ZrH$, $(Me_2Cp)_2(MeBuCp)ZrH$, $(Me_2CP)_2(Me_3Cp)ZrH$, $(Me_3Cp)_2(Cp)ZrH$, $(MeCp)_3ZrH$, $(EtCp)_3ZrH$, $(PrCp)_3ZrH$, $(BuCp)_3ZrH$, $(PhCp)_3ZrH$, $(Me_3SiCp)_3ZrH$, $(Et_3SiCp)_3ZrH$, $(Me_2Cp)_3ZrH$, $(Me_3Cp)_3ZrH$, $(Me_4Cp)_3ZrH$, $(Me_5Cp)_3ZrH$, $Ind_2(Cp)ZrH$, $Ind_2(MeCp)ZrH$, $Ind_2(PrCp)ZrH$, $Ind_2(BuCp)ZrH$, $Ind_2(Me_2Cp)ZrH$, $Ind_2(MePrCp)ZrH$, $Ind_2(MeBuCp)ZrH$, $Ind_2(Me_3SiCp)ZrH$, $Ind_2(Me_3Cp)ZrH$, $(Cp)(Ind)(MeCp)ZrH$, $(Cp)(Ind)(PrCp)ZrH$, $(Cp)(Ind)(BuCp)ZrH$, $(Cp)(Ind)(Me_2Cp)ZrH$, $(Cp)(Ind)(Me3SiCp)ZrH$, $(Cp)(Ind)(Me_3Cp)ZrH$, $MeInd_2(Cp)ZrH$, $MeInd_2(MeCp)ZrH$, $MeInd_2(PrCp)ZrH$, $MeInd_2(BuCp)ZrH$, $MeInd_2(Me_2Cp)ZrH$, $MeInd_2(Me_3SiCp)ZrH$, $MeInd_2(Me_3Cp)ZrH$, $(Cp)(MeInd)(MeCp)ZrH$, $(Cp)(MeInd)(PrCp)ZrH$, $(Cp)(MeInd)(BuCp)ZrH$, $(Cp)(MeInd)(Me_2Cp)ZrH$, $(Cp)(MeInd)(MePrCp)ZrH$, $(Cp)(MeInd)(MeBuCp)ZrH$, $(Cp)(MeInd)(Me_3SiCp)ZrH$, $(Cp)(MeInd)(Me_3Cp)ZrH$, $PhInd_2(Cp)ZrH$, $PhInd_2(MeCp)ZrH$, $PhInd_2(PrCp)ZrH$, $PhInd_2(BuCp)ZrH$, $PhInd_2(Me_2Cp)ZrH$, $PhInd_2(MePrCp)ZrH$, $PhInd_2(MeBuCp)ZrH$, $PhInd_2(Me_3SiCp)ZrH$, $PhInd_2(Me_3Cp)ZrH$, $(Cp)(PhInd)(MeCp)ZrH$, $(Cp)(PhInd)(PrCp)ZrH$, $(Cp)(PhInd)(BuCp)ZrH$, $(Cp)(PhInd)(Me_2Cp)ZrH$, $(Cp)(PhInd)(MePrCp)ZrH$, $(Cp)(PhInd)(MeBuCp)ZrH$, $(Cp)(PhInd)(Me_3SiCp)ZrH$, $(Cp)(PhInd)(Me_3Cp)ZrH$, $Me_4Ind_2(Cp)ZrH$, $Me_4Ind_2(MeCp)ZrH$, $Me_4Ind_2(PrCp)ZrH$, $Me_4Ind_2(BuCp)ZrH$, $Me_4Ind_2(Me_2Cp)ZrH$, $Me_4Ind_2(MePrCp)ZrH$, $Me_4Ind_2(MeBuCp)ZrH$, $Me_4Ind_2(Me_3SiCp)ZrH$, $Me_4Ind_2(Me_3Cp)ZrH$, $(Cp)(Me_4Ind)(MeCp)ZrH$, $(Cp)(Me_4Ind)(PrCp)ZrH$, $(Cp)(Me_4Ind)(BuCp)ZrH$, $(Cp)(Me_4Ind)(Me_2Cp)ZrH$, $(Cp)(Me_4Ind)(MePrCp)ZrH$, $(Cp)(Me_4Ind)(MeBuCp)ZrH$, $(Cp)(Me_4Ind)(Me_3SiCp)ZrH$, $(Cp)(Me_4Ind)(Me_3Cp)ZrH$, $BenzInd_2(Cp)ZrH$, $BenzInd_2(MeCp)ZrH$, $BenzInd_2(PrCp)ZrH$, $BenzInd_2(BuCp)ZrH$, $BenzInd_2(Me_2Cp)ZrH$, $BenzInd_2(MePrCp)ZrH$, $BenzInd_2(MeBuCp)ZrH$, $BenzInd_2(Me_3SiCp)ZrH$, $BenzInd_2(Me_3Cp)ZrH$, $(Cp)(BenzInd)(MeCp)ZrH$, $(Cp)(BenzInd)(PrCp)ZrH$, $(Cp)(BenzInd)(BuCp)ZrH$, $(Cp)(BenzInd)(Me_2Cp)ZrH$, $(Cp)(BenzInd)(MePrCp)ZrH$, $(Cp)(BenzInd)(MeBuCp)ZrH$, $(Cp)(BenzInd)(Me_3SiCp)ZrH$, $(Cp)(BenzInd)(Me_3Cp)ZrH$, $DibenzoInd_2(Cp)ZrH$, $DibenzoInd_2(MeCp)ZrH$, $DibenzoInd_2(PrCp)ZrH$, $DibenzoInd_2(BuCp)ZrH$, $DibenzoInd_2(Me_2Cp)ZrH$, $DibenzoInd_2(MePrCp)ZrH$, $DibenzoInd_2(MeBuCp)ZrH$, $DibenzoInd_2(Me_3SiCp)ZrH$, $DibenzoInd_2(Me_3Cp)ZrH$, $(Cp)(DibenzoInd)(MeCp)ZrH$, $(Cp)(DibenzoInd)(PrCp)ZrH$, $(Cp)(DibenzoInd)(BuCp)ZrH$, $(Cp)(DibenzoInd)(Me_2Cp)ZrH$, $(Cp)(DibenzoInd)(MePrCp)ZrH$, $(Cp)(DibenzoInd)(MeBuCp)ZrH$, $(Cp)(DibenzoInd)(Me_3SiCp)ZrH$, $(Cp)(DibenzoInd)(Me_3Cp)ZrH$, $Ind_3ZrH$, $Ind_2(MeInd)ZrH$, $Ind_2(EtInd)ZrH$, $Ind_2(PrInd)ZrH$, $Ind_2(BuInd)ZrH$, $Ind_2(Me_3SiInd)ZrH$, $Ind_2(Me_2Ind)ZrH$, $Ind_2(Et_2Ind)ZrH$, $Ind_2(Pr_2Ind)ZrH$, $Ind_2(Bu_2Ind)ZrH$, $Ind_2(Me_4Ind)ZrH$, $Ind_2(Et_4Ind)ZrH$, $Ind_2(Pr_4Ind)ZrH$, $Ind_2(Bu_4Ind)ZrH$, $Ind_2(NaphInd)ZrH$, $Ind_2(BiPhInd)ZrH$, $(MeInd)_3ZrH$, $(EtInd)_3ZrH$, $(PrInd)_3ZrH$, $(BuInd)_3ZrH$, $(Me_3SiInd)_3ZrH$, $(PhInd)_3ZrH$, $(NaphInd)_3ZrH$, $(BiPhInd)_3ZrH$, $(Me2Ind)3ZrH$, $(Et2Ind)_3ZrH$, $(Pr2Ind)3ZrH$, $(Bu_2Ind)_3ZrH$, $(Me_2Ind)_2(Ind)ZrH$, $(Et_2Ind)_2(Ind)ZrH$, $(Pr_2Ind)_2(Ind)ZrH$, $(Bu_2Ind)_2(Ind)ZrH$, $(Ph_2Ind)_2(Ind)ZrH$, $(Me_3Ind)_3ZrH$, $(Et_3Ind)_3ZrH$, $(Pr_3Ind)_3ZrH$, $(Bu_3Ind)_3ZrH$, $(Me_4Ind)_3ZrH$, $(Et_4Ind)_3ZrH$, $(Pr_4Ind)_3ZrH$, $(Bu_4Ind)_3ZrH$, $(BenzInd)_3ZrH$, $(BenzInd)_2(Ind)ZrH$, $(DibenzoInd)_2(Ind)ZrH$, and $(DibenzoInd)3ZrH$.

Among them, more preferable compounds as the components of catalyst for olefin polymerization are: $Cp_2(MeCp)ZrH$, $Cp_2(PrCp)ZrH$, $Cp_2(BuCp)ZrH$, $Cp_2(Me_2Cp)ZrH$, $Cp_2(Me_3SiCp)ZrH$, $Cp_2(Me_3Cp)ZrH$, $(MeCp)_2(Cp)ZrH$, $(MeCp)_2(PrCp)ZrH$, $(MeCp)_2(BuCp)ZrH$, $(MeCp)_2(Me_2Cp)ZrH$, $(MeCp)_2(Me_3SiCp)ZrH$, $(BuCp)_2(Cp)ZrH$, $(BuCp)_2(MeCp)ZrH$, $(BuCp)_2(PrCp)ZrH$, $(BuCp)_2(Me_2Cp)ZrH$, $BuCp)_2(Me_3SiCp)ZrH$, $(Me_3SiCp)_2(Cp)ZrH$, $(Me_3SiCp)_2(MeCp)ZrH$, $(Me_3SiCp)_2(Me_2Cp)ZrH$, $(Me_3SiCp)_2(Me_3Cp)ZrH$, $(Me_2Cp)_2(Cp)ZrH$, $(Me_2Cp)_2(MeCp)ZrH$, $(Me_2Cp)_2(MePrCp)ZrH$, $(Me_2Cp)_2(MeBuCp)ZrH$, $(Me_2Cp)_2(Me_3Cp)ZrH$, $(Me_3Cp)_2(Cp)ZrH$, $(MeCp)_3ZrH$, $(PrCp)_3ZrH$, $(BuCp)_3ZrH$, $(Me_3SiCp)_3ZrH$, $(Me_2Cp)_3ZrH$, $(Me_3Cp)_3ZrH$, $Ind_2(Cp)ZrH$, $Ind_2(MeCp)ZrH$, $Ind_2(PrCp)ZrH$, $Ind_2(BuCp)ZrH$, $Ind_2(Me_2Cp)ZrH$, $Ind_2(MePrCp)ZrH$, $Ind_2(MeBuCp)ZrH$, $Ind_2(Me_3SiCp)ZrH$, $Ind_2(Me_3Cp)ZrH$, $BenzInd_2(Cp)ZrH$, $BenzInd_2(MeCp)ZrH$, $BenzInd_2(PrCp)ZrH$, $BenzInd_2(BuCp)ZrH$, $BenzInd_2(Me_2Cp)ZrH$, $BenzInd_2(MePrCp)ZrH$, $BenzInd_2(MeBuCp)ZrH$, $BenzInd_2(Me_3SiCp)ZrH$, $BenzInd_2(Me_3Cp)ZrH$, $Ind_3ZrH$, $Ind_2(Me_2Ind)ZrH$, $Ind_2(Et_2Ind)ZrH$, $Ind_2(Pr_2Ind)ZrH$, $Ind_2(Bu_2Ind)ZrH$, $Ind_2(Me_4Ind)ZrH$, $Ind_2(Et_4Ind)ZrH$, $Ind_2(Pr_4Ind)ZrH$, $Ind_2(Bu_4Ind)ZrH$, $Ind_2(NaphInd)ZrH$, $Ind_2(BiPhInd)ZrH$, $(PhInd)_3ZrH$, $(NaphInd)_3ZrH$, $(BiPhInd)_3ZrH$, $(Me_2Ind)_3ZrH$, $(Et_2Ind)_3ZrH$, $(Pr_2Ind)_3ZrH$, $(Bu_2Ind)_3ZrH$, $(Me_4Ind)_3ZrH$, $(Et_4Ind)_3ZrH$, $(Pr_4Ind)_3ZrH$, $(Bu_4Ind)_3ZrH$, $(BenzInd)_3ZrH$, $(BenzInd)_2(Ind)ZrH$ and $(DibenzoInd)_3ZrH$.

The examples of transition metal compounds of the present invention that are represented by the foregoing general formula (5) are shown in the following.

That is, $Ind_3ZrH$, $Ind_2(MeInd)ZrH$, $Ind_2(EtInd)ZrH$, $Ind_2(PrInd)ZrH$, $Ind_2(BuInd)ZrH$, $Ind_2(Me_3SiInd)ZrH$, $Ind_2(Me_2Ind)ZrH$, $Ind_2(Et_2Ind)ZrH$, $Ind_2(Pr_2Ind)ZrH$, $Ind_2(Bu_2Ind)ZrH$, $Ind_2(Me_4Ind)ZrH$, $Ind_2(Et_4Ind)ZrH$, $Ind_2(Pr_4Ind)ZrH$, $Ind_2(Bu_4Ind)ZrH$, $Ind_2(NaphInd)ZrH$, $Ind_2(BiphInd)ZrH$, $(MeInd)_3ZrH$, $(EtInd)_3ZrH$, $(PrInd)_3ZrH$, $(BuInd)_3ZrH$, $(Me_3SiInd)_3ZrH$, $(PhInd)_3ZrH$, $(NaphInd)_3ZrH$, $(BiPhInd)_3ZrH$, $(Me_2Ind)_3ZrH$, $(Et_2Ind)_3ZrH$, $(Pr_2Ind)_3 ZrH$, $(Bu_2Ind)_3ZrH$, $(Me_2Ind)_2(Ind)ZrH$, $(Et_2Ind)_2(Ind)ZrH$, $(Pr_2Ind)_2(Ind)ZrH$, $(Bu_2Ind)_2(Ind)ZrH$, $(Ph_2Ind)_2(Ind)ZrH$, $(Me_3Ind)_3ZrH$, $(Et_3Ind)_3ZrH$, $(Pr_3Ind)_3ZrH$, $(Bu_3Ind)_3ZrH$, $(Me_4Ind)_3ZrH$, $(Et_4Ind)_3ZrH$, $(Pr_4Ind)_3ZrH$, $(Bu_4Ind)_3ZrH$, $(BenzInd)_3ZrH$, $(BenzInd)_2(Ind)ZrH$, $(BenzInd)(Ind)_2ZrH$, $(DibenzoInd)_2(Ind)ZrH$, $(DibenzoInd)(Ind)_2 ZrH$, $(DibenzoInd)_3ZrH$, $(BenzInd)_2(DibenzoInd)ZrH$, $(BenzInd)(DibenzoInd)_2ZrH$ and $(DibenzoInd)(BenzInd)(Ind)ZrH$.

The abbreviations for the groups in the above structural formulae are the same as defined in the forgoing passage.

It is possible to use two or more of these compounds as the components of catalyst for olefin polymerization.

Among the above examples, preferable compounds as the components of the catalyst for olefin polymerization are exemplified by: $Ind_3ZrH$, $Ind_2(Me_2Ind)ZrH$, $Ind_2(Et_2Ind)ZrH$, $Ind_2(Pr_2Ind)ZrH$, $Ind_2(Bu_2Ind)ZrH$, $Ind_2(Me_4Ind)ZrH$, $Ind_2(Et_4Ind)ZrH$, $Ind_2(Pr_4Ind)ZrH$, $Ind_2(Bu_4Ind)ZrH$, $Ind_2(NaphInd)ZrH$, $Ind_2(BiPhInd)ZrH$, $(PhInd)_3ZrH$, $(NaphInd)_3ZrH$, $(BiPhInd)_3ZrH$, $(Me_2Ind)_3ZrH$, $(Et_2Ind)_3ZrH$, $(Pr_2Ind)_3ZrH$, $(Bu_2Ind)_3ZrH$, $(Me_4Ind)_3ZrH$, $(Et_4Ind)_3ZrH$, $(Pr_4Ind)_3ZrH$, $(Bu_4Ind)_3ZrH$, $(BenzInd)_3ZrH$, $(BenzInd)(Ind)_2ZrH$, $(DibenzoInd)_2(Ind)ZrH$, $(DibenzoInd)(Ind)_2ZrH$, $(DibenzoInd)_3ZrH$, $(BenzInd)_2(DibenzoInd)ZrH$, $(BenzInd)(DibenzoInd)_2ZrH$ and $(DibenzoInd)(BenzInd)(Ind)ZrH$.

Among the above examples, more preferable compounds as the components of the catalyst for olefin polymerization are: $Ind_3ZrH$, $(MeCp)(Cp)_2ZrH$, $(Me_3SiCp)(Cp)_2ZrH$, $(Me_3SiCp)_3ZrH$, $(MeCp)_3ZrH$, $(1,3\text{-}Me_2Cp)_3ZrH$, $Ind(1,3\text{-}Me_2Cp)_2ZrH$, $(1\text{-}Me\text{-}3\text{-}PrCp)_3ZrH$, $(BenzInd)_3ZrH$ and $(DibenzoInd)_3ZrH$.

The exemplar processes for synthesizing novel transition metal compounds according to the present invention are described in the following as Synthetic Methods 1 and 2. It should be noted, however, that the present invention is not limited to these methods.

<Synthetic Method 1>
1) Preparation by bringing the following compounds of a), b) and c) into contact.
   a) $(C_5R^{77}R^{78}R^{79}R^{80}R^{81})(C_5R^{82}R^{83}R^{84}R^{85}R^{86})M^7X^1_2$
   b) $C_5HR^{87}R^{88}R^{89}R^{90}R^{91}$
   c) $LiR^{92}$ In the above formulae, $C_5R^{77}R^{78}R^{79}R^{80}R^{81}$ and $C_5R^{82}R^{83}R^{84}R^{85}R^{86}$ denote cyclopentadienyl groups or substituted cyclopentadienyl groups, respectively, and $C_5HR^{87}R^{88}R^{89}R^{90}R^{91}$ denotes cyclopentadiene or substituted cyclopentadiene. $R^{77}$, $R^{78}$, $R^{79}$, $R^{80}$, $R^{81}$, $R^{82}$, $R^{83}$, $R^{84}$, $R^{85}$, $R^{86}$, $R^{87}$, $R^{88}$, $R^{89}$, $R^{90}$ and $R^{91}$ are similar to the groups of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ in the novel transition metal compound of the present invention represented by the foregoing general formula (1). $X^1$ denotes fluorine, chlorine, bromine or iodine. Two $(X^1)$'s may be the same or different from each other. As $X^1$, chlorine and bromine are preferable, and chlorine is more desirable. $R^{92}$ denotes an alkyl group such as ethyl group, propyl group, butyl group or hexyl group. These groups can be branched ones. n-Butyl group is preferable one.

When compounds a), b) and c) are brought into contact together, it is ordinarily carried out under the atmosphere of inert gas such as nitrogen or. argon and generally in the presence of an aromatic hydrocarbon, liquid inert hydrocarbon or oxygen-containing hydrocarbon solvent, with or without stirring. As the liquid inert hydrocarbons, aromatic hydrocarbons such as benzene, toluene, xylene or ethylbenzene are used, and aliphatic or alicyclic hydrocarbons such as heptane, hexane, decane, dodecane and cyclohexane are used. As the oxygen-containing hydrocarbon solvents, diethyl ether and tertahydrofuran are used.

The order of contacting is not limited especially, however, the practical contacting process is preferably carried out as follows, that is, after bringing a compound a) into contact with a compound c), the compound b) is brought into contact.

In the contacting process, all compounds may be subjected to reaction simultaneously or they are brought into contact slowly or step by step over a period of a certain time. Furthermore, contacting of compounds can be carried out in plurality of processes.

The contacting of compound a) with compound c) is desirably carried out at temperatures in the range of −100 to 0° C., preferably at −80 to −40° C., and for a period of 5 minutes to 24 hours, preferably for 30 minutes to 3 hours. After that, the temperature is raised to −30 to 30° C., preferably about 0 to 10° C., and a halogenated alkali metal such as LiCl generated in this step is removed by filtration. Subsequently, after the compound b) is brought into contact with them, the reaction product is stirred for a period of 5 minutes to 3 days, preferably for 1 hour to 24 hours, at a temperature in the range of 0° C. to 150° C., preferably in the range of 20° C. to 80° C. After the solvent is removed from the solution of reaction, it is rinsed with an aliphatic hydrocarbon such as pentane or hexane to obtain the novel transition metal compound of the present invention.

It is also possible that, after compounds a), b) and c) are brought into reaction and heated with stirring, LiCl is removed the reaction solution by filtration from the liquid inert hydrocarbon solution of aromatic hydrocarbon such as benzene, toluene, xylene or ethylbenzene, or aliphatic or alicyclic hydrocarbon such as heptane, hexane, decane, dodecane or cyclohexane. Furthermore, it is also possible that, after the removal of solvent from the reaction solution, LiCl is removed by rinsing with oxygen-containing hydrocarbon solvent such as tetrahydrofuran.

The ratios of the compounds are such that, relative to 1 mol of compound a), 1 to 50 mol, preferably 2 to 8 mol, of compound b) is used and generally 2 mol of compound c) is used.

<Synthetic Method 2>
1) Preparation by bringing the following compound d) into contact with the following compound e).
   d) $Ind_3ZrH$
   e) $C_5HR^{93}R^{94}R^{95}R^{96}R^{97}$ In the above formulae, $C_5HR^{93}R^{94}R^{95}R^{96}R^{97}$ denotes cyclopentadiene or substituted cyclopentadiene. $R^{93}$, $R^{94}$, $R^{95}$, $R^{96}$ and $R^{97}$ are similar to $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ of the novel transition metal compound of the present invention represented by the general formula (1).

When the compound d) is brought into contact with the compound e), the process is usually carried out under the atmosphere of inert gas such as nitrogen or argon in the presence of a solvent of aromatic hydrocarbon, liquid inert hydrocarbon or oxygen-containing hydrocarbon with or without stirring. As the aromatic hydrocarbon, benzene, toluene, xylene or ethylbenzene is generally used, and as the inert liquid hydrocarbon, aliphatic or alicyclic hydrocarbon such as heptane, hexane, decane, dodecane or cyclohexane is generally used. As the oxygen-containing hydrocarbon solvent, diethyl ether or tertahydrofuran is used.

Contacting of the compound d) and compound e) is usually carried out at a temperature in the range of −80 to 150° C., preferably 0 to 50° C., and for a time length of 1 minute to 3 hours, preferably for 10 minutes to 1 hour. After that, the reaction solution is heated to a temperature in the range of 0 to 150° C., preferably about 20 to 110° C. and subjected to stirring for 5 minutes to 3 days, preferably 1 hour to 24 hours. The solvent is then removed from the reaction solution, and the resultant product is rinsed with an aliphatic hydrocarbon such as pentane or hexane, thereby obtaining the novel transition metal compound of the present invention (1).

The ratio of the compound e) to be used may be 1 to 50 mol, preferably 2 to 8 mol, for 1 mol of the compound d).

Ind$_3$ZrH of compound d) can be obtained by the foregoing Synthetic Method 1.

The novel transition metal compound proposed by the present invention can be used as a catalyst for olefin polymerization by combining with the following organoaluminum oxy compound, or with a compound that is reactive with the novel transition metal compound to generate ion pairs, or with the mixture of them.

The organoaluminum oxy compound has "Al—O—Al" bond in the molecule. The number of the bonds is usually in the range of 1 to 100, preferably 1 to 50. The organoaluminum oxy compound is generally produced through the reaction of organoaluminum compound with water. The reaction of organoaluminum compound with water is carried out in an inert hydrocarbon. As the inert hydrocarbon, aliphatic hydrocarbon, alicyclic hydrocarbon and aromatic hydrocarbon, such as pentane, hexane, heptane, cyclohexane, methylcyclohexane, benzene, toluene or xylene, can be used. Among them, an aliphatic hydrocarbon or an aromatic hydrocarbon is preferable.

As the organoaluminum compound used for preparing the organoaluminum oxy compound, any of compounds represented by the following general formula (7) may be employed. Among them, trialkylaluminum compound is preferably used.

  Formula (7)

$$R^{98}{}_tAlX^2{}_{3-t}$$

(In the above formula, R$^{98}$ denotes a hydrocarbon group such as alkyl group, alkenyl group, aryl group or aralkyl group, which has 1 to 18 carbon atoms, preferably 1 to 12 carbon atoms. X$^2$ denotes hydrogen atom or halogen atom. The symbol t denotes an integer of $1 \leq t \leq 3$.)

The alkyl group of the above trialkylaluminum compound may also be any one of methyl group, ethyl group, propyl group, isopropyl group, butyl group, isobutyl group, pentyl group, hexyl group, octyl group, decyl group and dodecyl group. Among them, the methyl group is especially preferable.

The above organoaluminum compounds can also be used in a mixture of two or more kinds.

The ratio of water to the organoaluminum compound (molar ratio of water/Al) in the reaction is preferably 0.25/1 to 1.2/1 and more preferably 0.5/1 to 1/1. The reaction temperature is generally in the range of −70 to 100° C., preferably −20 to 20° C. The retention time of the reaction is generally selected from the range of 5 minutes to 24 hours, preferably 10 minutes to 5 hours. As the water content in the reaction, it is also possible to use not only the mere water but also the crystal water contained in copper sulfate hydrate or aluminum sulfate hydrate. Furthermore, the water generated in the reaction system can also be available.

Among the above organoaluminum oxy compounds, those obtained from the reaction of alkylaluminum with water is preferable, which is generally called as aluminoxane. The methylaluminoxane (including those substantially consisting of methylaluminoxane (MAO)) is more preferable as the organoaluminum oxy compound.

As the organoaluminum oxy compound, the above organoaluminum oxy compounds may be used in a combination of two or more kinds. The above organoaluminum oxy compounds can be used as a solution that is dissolved or dispersed in the above-mentioned inert hydrocarbon solvent.

The exemplar compounds to generate ion pairs by the reaction with the novel transition metal compound are borane compounds and borate compounds.

More particularly, the borane compounds are exemplified by triphenylborane, tri(o-tolyl)borane, tri(p-tolyl)borane, tri (m-tolyl)borane, tris(o-fluorophenyl)borane, tris(p-fluorophenyl)borane, tris(m-fluorophenyl)-borane, tris(2,5-difluorophenyl)borane, tris(3,5-difluotrophenyl)borane, tris(4-trifluoromethylphenyl)borane, tris(3,5-ditrifluoromethylphenyl)borane, tris(2,6-ditrifluoromethylphenyl)borane, tris(pentafluorophenyl) borane, tris(perfluoronaphthyl)borane, tris (perfluorobiphenyl)borane, tris(perfluoro-anthryl)borane and tris(perfluorobinaphthyl)borane.

Among these compounds, preferable compound are exemplified by tris(3,5-ditrifluoromethylphenyl)borane, tris (2,6-ditrifluoromethylphenyl)-borane, tris(pentafluorophenyl)borane, tris(perfluoronaphthyl)borane, tris-(perfluorobiphenyl)borane, tris(perfluoroanthryl)borane and tris (perfluorobinaphthyl)borane. More preferable compounds are exemplified by tris(2,6-ditrifluoromethylphenyl)borane, tris(pentafluorophenyl)borane, tris(perfluoronaphthyl)borane and tris(perfluorobiphenyl)borane.

Particular first examples of the borate compounds are represented by the following general formula (8).

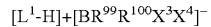  Formula (8)

$$[L^1\text{-}H]^+[BR^{99}R^{100}X^3X^4]^-$$

In the formula, L$^1$ is a neutral Lewis base, H is hydrogen atom and [L$^1$-H] is a Brønsted acid such as ammonium, anilinium or phosphonium. The ammonium is exemplified by trialkyl-substituted ammonium such as trimethylammonium, triethylammonium, tripropylammonium, tributylammonium or tri(n-butyl)ammonium, and dialkylammonium such as di(n-propyl)ammonium or dicyclohexylammonium.

As the aniliniums, N,N-dialkyl anilinium such as N,N-dimethyl anilinium, N,N-diethyl anilinium and N,N-2,4,6-pentamethyl anilinium are exemplified. Furthermore, as the phosphoniums, triarylphosphonium and trialkylarylphosphonium, such as triphenylphosphonium, tributylphosphonium, tri(methylphenyl)phosphonium and tri(dimethylphenyl)phosphonium are exemplified.

R$^{99}$ and R$^{100}$ are aromatic hydrocarbon groups or substituted aromatic hydrocarbon groups each having 6 to 20, preferably 6 to 16, carbon atoms, which are the same or difference from each other. They can be bonded to each other through cross-linking groups. As preferable substituents of the substituted aromatic group, alkyl group represented by methyl group, ethyl group or propyl group, and halogen atom such as fluorine, chlorine, bromine or iodine are exemplified.

X$^3$ and X$^4$ are any one of hydride group, halide group, hydrocarbyl group having 1 to 20 carbon atoms and substituted hydrocarbyl group having 1 to 20 carbon atoms, in which one or more hydrogen atoms are replaced by halogen atom or atoms.

The actual examples of the compound represented by foregoing general formula (8) are tributylammoniumtetra (pentafluorophenyl)borate, tributylammoniumtetra(2,6-ditrifluoromethylphenyl)borate, tributylammoniumtetra(3, 5-ditrifluoromethylphenyl)borate, tributylammoniumtetra (2,6-difluorophenyl)borate, tributylammoniumtetra (perfluoronaphthyl)borate, dimethylaniliniumtetra (pentafluoronaphthyl)borate, dimethylaniliniumtetra(2,6-ditrifluoromethylphenyl)borate, dimethylaniliniumtetra(3,5-ditrifluoromethylphenyl)borate, dimethylaniliniumtetra(2,6-difluorophenyl)borate, dimethylaniliniumtetra (perfluoronaphthyl)borate, triphenylphosphoniumtetra (pentafluorophenyl)borate, triphenylphosphoniumtetra(2,6-ditrifluoromethylphenyl)borate, triphenylphosphoniumtetra(3,5-ditrifluoromethylphenyl)borate, triphenylphosphoniumtetra(2,6-ifluorophenyl)borate, triphenylphosphoniumtetra(perfluoronaphthyl)borate, trimethylammoniumtetra(2,6-ditrifluoromethylphenyl)borate, triethylammoniumtetra(pentafluorophenyl)borate, triethylammoniumtetra(2,6-ditrifluoromethylphenyl)borate, triethylammoniumtetra(perfluo-ronaphthyl)borate, tripropylammoniumtetra(pentafluorophenyl)borate, tripropylammoniumtetra(2,6-ditrifluoromethylphenyl)borate, tripropylammoniumtetra(perfluoronaphthyl)borate, di(1-propyl)ammoniumtetra(pentafluorophenyl)borate and dicyclohexylammoniumtetraphenylborate.

Examples of more preferable compounds among them are tributylammoniumtetra(pentafluorophenyl)borate, tributylammoniumtetra(2,6-ditrifluoromethylphenyl)borate, tributylammoniumtetra(3,5 -ditrifluoromethylphenyl)borate, tributylammoniumtetra(perfluoronaphthyl)borate, dimethylaniliniumtetra(pentafluorophenyl)borate, dimethylaniliniumtetra(2,6-ditrifluoromethylphenyl)borate, dimethylaniliniumtetra(3,5-ditrifluoromethylphenyl)borate and dimethylaniliniumtetra(perfluoronaphthyl)borate.

The second examples of the borate compounds are represented by the following general formula (9).

$$[L^2]^+[BR^{101}R^{102}X^5X^6]^-$$  Formula (9)

The symbol $L^2$ in the above formula is exemplified by carbo-cation, methyl cation, ethyl cation, propyl cation, isopropyl cation, butyl cation, isobutyl cation, tert-butyl cation, pentyl cation, tropenium cation, benzyl cation, trityl cation, sodium cation and proton. The definitions for $R^{101}$, $R^{102}$, $X^5$ and $X^6$ are the same as those for $R^{99}$, $R^{100}$, $X^3$ and $X^4$ in the above general formula (8).

Particular examples for the above compounds are trityltetraphenylborate, trityltetra(o-tolyl)borate, trityltetra(p-tolyl)borate, trityltetra(m-tolyl)-borate, trityltetra(o-fluorophenyl)borate, trityltetra(p-fluorophenyl)borate, trityltetra(m-fluorophenyl)borate, trityltetra(3,5-difluorophenyl)borate, trityltetra(pentafluorophenyl)borate, trityltetra(2,6-ditrifluoromethylphenyl)borate, trityltetra(3,5-ditrifluoromethylphenyl)borate, trityltetra(perfluoronaphthyl)borate, tropeniumtetraphenylborate, tropeniumtetra(o-tolyl)borate, tropeniumtetra(p-tolyl)borate, tropeniumtetra(m-tolyl)borate, tropeniumtetra(o-fluorophenyl)borate, tropeniumtetra(p-fluorophenyl)borate, tropeniumtetra(m-fluorophenyl)borate, tropeniumtetra(3,5-difluorophenyl)borate, tropeniumtetra(pentafluorophenyl)borate, tropeniumtetra(2,6-ditrifluoromethylphenyl)borate, tropeniumtetra(3,5-ditrifluoromethylphenyl)borate, tropeniumtetra-(perfluoronaphthyl)borate, $NaBPh_4$, $NaB(o—CH_3—Ph)_4$, $NaB(p—CH_3—Ph)_4$, $NaB(m—CH_3—Ph)_4$, $NaB(o—F—Ph)_4$, $NaB(p—F—Ph)_4$, $NaB(m—F—Ph)_4$, $NaB(3,5-F_2—Ph)_4$, $NaB(C_6F_5)_4$, $NaB(2,6-(CF_3)_2—Ph)_4$, $NaB(3,5-(CF_3)_2—Ph)_4$, $NaB(C_{10}F_7)_4$, $H^+BPh_4^-$-2-diethyl ether, $H^+B(3,5-F_2—Ph)_4$-2-diethyl ether, $H^+B(C_6F_5)_4^-$-2-diethyl ether, $H^+B(2,6-(CF_3)_2—Ph)_4$-2-diethyl ether, $H^+B(3,5-(CF_3)_2—Ph)_4$-2-diethyl ether and $H^+B(C_{10}H_7)_4$-2-diethyl ether.

Examples of preferable compounds among them are trityltetra-(pentafluorophenyl)borate, trityltetra(2,6-ditrifluoromethylphenyl)borate, trityltetra(3,5-ditrifluoromethylphenyl)borate, trityltetra(perfluoronaphthyl)-borate, tropeniumtetra(pentafluorophenyl)borate, tropeniumtetra(2,6-ditrifluoromethylphenyl)borate, tropeniumtetra(3,5-ditrifluoromethylphenyl)-borate, tropeniumtetra(perfluoronaphthyl)borate, $NaB(C_6F_5)_4$, $NaB(2,6-(CF_3)_2—Ph)_4$, $NaB(3,5-(CF_3)_2—Ph)_4$, $NaB(C_{10}F_7)_4$, $H^+B(C_6F_5)_4^-$-2-diethyl ether, $H^+B(2,6-(CF_3)_2—Ph)_4$-2-diethyl ether, $H^+B(3,5-(CF_3)_2—Ph)_4$-2-diethyl ether and $H^+B(C_{10}H_7)_4$-2-diethyl-ether.

More preferable ones are trityltetra(pentafluorophenyl)borate, trityltetra(2,6-ditrifluoromethylphenyl)borate, tropeniumtetra-(pentafluorophenyl)borate, tropeniumtetra(2,6-ditrifluoromethylphenyl)borate, $NaB(C_6F_5)_4$, $NaB(2,6-(CF_3)_2—Ph)_4$, $H^+B(2,6-(CF_3)_2—Ph)_4$-2-diethyl ether, $H^+B(3,5-(CF_3)_2—Ph)_4$-2-diethyl ether and $H^+B(C_{10}F_7)_4$-2-diethyl ether.

The catalyst for olefin polymerization, which is composed of the novel transition metal compound of present invention, the organoaluminum oxy compound and the compound being reactive with the novel transition metal compound to generate ion pairs, or their mixture, can be used as a solid catalyst by supporting the composition on a carrier.

As the carrier, an inorganic carrier, a granular polymeric carrier or their mixture can be used. As the inorganic carriers, metals, metallic oxides, metallic chlorides, metallic carbonates, carbonaceus substances or their mixtures can be used.

The metals preferably used for the inorganic carrier are exemplified by iron, aluminum and nickel.

Single oxides or double oxides of the element of groups 1 to 14 of the periodic table can be used as the metallic oxides. They are exemplified by various natural or synthetic single or double oxides such as $SiO_2$, $Al_2O_3$, $MgO$, $CaO$, $B_2O_3$, $TiO_2$, $ZrO_2$, $Fe_2O_3$, $Al_2O_3$—$MgO$, $Al_2O_3$—$CaO$, $Al_2O_3$-$SiO_2$, $Al_2O_3$—$MgO$—$CaO$, $Al_2O_3$—$MgO$—$SiO_2$, $Al_2O_3$—$CuO$, $Al_2O_3$—$Fe_2O_3$, $Al_2O_3$—$NiO$ or $SiO_2$—$MgO$. Incidentally, these chemical formulae are not intended to indicate molecular structure but only indicate the compositions of the usable compounds. It should be noted that the structures and compositions of the metallic oxides in the present invention are not limited by the above description.

The metallic oxides used in the present invention are allowed to absorb a small quantity of water or impurities without causing any disadvantage.

It is preferable to use chloride of alkali metal or alkaline earth metal as the metallic chloride. For example, $MgCl_2$ and $CaCl_2$ are particularly preferable.

As the metallic carbonates, the carbonate of alkali metal or carbonate of alkaline earth metal are preferably used. More particularly, magnesium carbonate, calcium carbonate and barium carbonate are exemplified.

As the carbonaceous substance, carbon black and activated carbon are exemplified. Although the above-mentioned inorganic carriers can be used, the foregoing metallic oxides, silica and alumina are preferable.

It is desirable that the inorganic carrier is used by adjusting the amount of hydroxyl group on the surface to 0.8 to 1.5 m-mol/g by baking it in an atmosphere of air or an inert gas such as nitrogen or argon at a temperature generally in the range of 200 to 800° C., preferably 460 to 600° C.

The properties of inorganic carrier are not especially limited, however, it is advisable to use an inorganic carrier having the properties of average diameter of generally 5 to 200 μm, preferably 10 to 150 μm; specific surface area of 150 to 1000 m²/g, preferably 200 to 500 m²/g; micro-pore volume of 0.3 to 2.5 cm³/g, preferably 0.5 to 2.0 cm³/g; and apparent specific gravity of 0.20 to 0.50 g/cm³, preferably 0.25 to 0.45 g/cm³.

Although the above-mentioned inorganic carrier can be used as it stands, it can also be used after pre-treatment to bring it into contact with organoaluminum compound, such as trimethylaluminum, triethylaluminum, triisobutylaluminum, trihexylaluminum, tripropylaluminum, tributylaluminum, trioctylaluminum, tridecylaluminum or diisobutylaluminum halide, or organoaluminum oxy compound containing Al—O—Al bonds.

In order to prepare the catalyst for olefin polymerization of the present invention, there is no limitation concerning the contacting method, in which the novel transition metal compound is brought into contact with an organoaluminum oxy compound, a compound being reactive with the novel transition metal compound to generate ion pairs or their mixture, and with the carrier. It is, however, possible to employ optionally the following methods.

(I) The novel transition metal compound, organoaluminum oxy compound, the compound that is reactive with the novel transition metal compound to generate ion pairs are brought into contact with one another, and subsequently the reaction product is brought into contact with the carrier.

(II) The novel transition metal compound and the carrier are brought into contact together, and subsequently the reaction product is brought into contact with organoaluminum oxy compound, the compound that is reactive with the novel transition metal compound to generate ion pairs.

(III) The organoaluminum oxy compound, the compound being reactive with the novel transition metal compound to generate ion pairs are brought into contact with the carrier, and subsequently they are brought into contact with the novel transition metal compound.

Among these processes, the above (I) and (III) are preferable. In any contacting method, the respective reactants are usually brought into contact together under an inert atmosphere such as nitrogen or argon, in the presence of a liquid inert hydrocarbon such aromatic hydrocarbons (usually those having 6 to 12 carbon atoms) such as benzene, toluene, xylene and ethylbenzene, or aliphatic or alicyclic hydrocarbons (having of 5 to 12 carbon atoms) such as heptane, hexane, decane, dodecane and cyclohexane, with or without stirring.

It is generally desirable to carry out this contacting at a temperature in the range of −100° C. to 200° C., preferably −50° C. to 100° C., and for a retention time of 10 minutes to 50 hours, preferably 1 to 24 hours.

In the contacting process of the novel transition metal compound, the organoaluminum oxy compound, the compound being reactive with the novel transition metal compound to generate ion pairs, with the carrier, any aromatic hydrocarbon solvent in which a certain component is soluble or slightly soluble and an aliphatic or alicyclic hydrocarbon solvent in which a certain component is insoluble or slightly soluble, can be used.

When the contacting of the respective components is carried out stepwise, just the solvent as used in the preceding step can be used as the solvent in the subsequent step without removing it. When a solvent of large dissolving power is used in the preceding step of contacting, a poor solvent of liquid inert hydrocarbon, in which a certain component is difficultly soluble or in soluble (e.g., aliphatic hydrocarbon, alicyclic hydrocarbon or aromatic hydrocarbon such as pentane, hexane, decane, dodecane, cyclohexane, benzene, toluene or xylene) may be added in the subsequent step, and after desired product is recovered as a solid substance, the desired product is subjected to the next contacting step by using any of the above-mentioned inert hydrocarbon solvent. Otherwise, after desired product is recovered as a solid substance by removing a part or all of the solvent of good dissolving power by drying, the desired product is subjected to the subsequent contacting step. In the present invention, the any component may be brought into a plurality of contacting processes.

As the ratio of the novel transition metal compound to the organo-aluminum oxy compound, or the novel transition metal compound to the compound being reactive with the transition metal compound to generate ion pairs and carrier, the following range is desirable, although there is no limitation.

In the case that organoaluminum oxy compound is used, the ratio of elements of aluminum of the organoaluminum oxy compound to the transition metal (M) of the novel transition metal compound, (Al/M), is generally in the range of 1 to 100,000, preferably 5 to 1000, and more preferably 50 to 200. In the case that the compound being reactive with the novel transition metal compound to generate ion pairs is used, the ratio of elements of boron to the transition metal of the novel transition metal compound, (B/M), is generally selected from the range of 0.01 to 100 (by mol), preferably 0.1 to 50 (by mol), and more preferably 0.2 to 10 (by mol).

The carrier of 1 g is used for 0.0001 to 5 mmol of the transition metal in the novel transition metal compound, preferably for 0.001 to 0.5 mmol, and more preferably for 0.01 to 0.1 mmol.

The novel transition metal compound, the organoaluminum oxy compound, the compound that is reactive with the novel transition metal compound to generate ion pairs and carrier are brought into contact through any one of the above-mentioned processes of (I) to (III), and by the removal of solvent, the solid state catalyst compound for olefin polymerization can be obtained. The removal of solvent is carried out under atmospheric pressure or reduced pressure at a temperature in the range of 0 to 200° C., preferably at 20 to 150° C. for a reaction time of 1 minute to 50 hours, more preferably for 10 minutes to 10 hours.

Furthermore, the catalyst compound for olefin polymerization can also be obtained by the following procedure.

(IV) The novel transition metal compound and the carrier are brought into contact together, and after the removal of solvent, solid catalyst components are obtained. The solid catalyst components are brought into contact with the organoaluminum oxy compound and the compound that is reactive with the novel transition metal compound to generate ion pairs, under polymerizing condition.

(V) The organoaluminum oxy compound, the compound that is reactive with the novel transition metal compound to generate ion pairs and the carrier are brought into contact together, and after removal of solvent solid catalyst components are obtained. The solid catalyst components are used as the novel catalyst components under polymerizing conditions.

In the above contacting processes of (IV) and (V), the ratios of components, contacting conditions and conditions for removing solvent may be the same as the forgoing processes.

The novel transition metal compound can also be used as a catalyst by supporting it on layered silicate.

The layered silicate is the compound having a crystal structure that is composed by laying crystal planes formed by ionic bonds into parallel layers to overlap one another by weak bonding force.

Although most layered silicates are obtained from natural resources as the main components of clay minerals, they are not limited to the natural products but they are available as artificial products.

Among them, smectite group minerals such as montmorillonite, sauconite, beidellite, nontronite, saponite, hectorite, stevensite, bentonite or taeniolite, and vermiculite group and mica group are preferable.

The natural products often have no ion-exchange capacity and no swelling property. In such a case, it is preferable to subject them to the treatment to impart ion-exchange capacity (or swelling property) in order to convert them having good ion-exchange capacity (or swelling property). The particularly preferable treatment for such purpose is the following chemical treatment. In the chemical treatment as employed are the surface treatment to remove impurities on their surfaces and the treatment to change crystal structure or chemical composition of the layered silicate. More particularly, they are exemplified by (a) acid treatment by using hydrochloric acid, sulfuric acid or the like; (b) alkali treatment by using NaOH, KOH, $NH_3$ or the like; (c) salt treatment by using salts composed of a cation containing at least one member selected from the group 2 to 14 of the periodic table and at least one member of an anion selected from halogen and anion of inorganic acid origin; and (iv) organic substance treatment by using alcohol hydrocarbon compound, formaldehyde, aniline or the like. These treatments can be applied singly or in combination of two or more.

The properties of the above-mentioned layered silicate particles can be adjusted by means of milling, granulation, classification, fractionation and so forth, at any step of before, during or after the treatments. Any method can be applied at will as far as it meets the purpose of process. Particularly, examples of granulation among these methods are spray granulation, roll granulation, compression granulation, stirring granulation, briquetting granulation, compacting granulation, extrusion granulation, fluidized bed granulation, emulsion granulation, and submerged granulation. More preferable methods among them are exemplified by spray granulation, roll granulation and compression granulation.

Although the above-mentioned layered silicate is used as it stands, they can also be used in combination with an organoaluminum compound such as trimethylaluminum, triethylaluminum, triisobutylaluminum, tripropylaluminum, tributylaluminum, trihexylaluminum, trioctylaluminum, tridecylaluminum or diisobutylaluminumhydride, and an organoaluminum oxy compound containing Al—O—Al bond.

In order to support the novel transition compound on the layered silicate, the transition metal compound and the layered silicate are brought into contact with each other, otherwise the transition metal compound, the organoaluminum compound and the layered silicate are brought into contact together. There is no limitation concerning the contacting method of the components, especially. For example, the following processes are employed optionally.

(VI) After the contacting of the novel transition metal compound and the organoaluminum compound, the obtained reaction product is brought into contact with the layered silicate.

(VII) After the contacting of the novel transition metal compound and the carrier, the obtained product is brought into contact with the organoaluminum compound.

(VIII) After the contacting of the ogranoaluminum oxy compound and the carrier, the obtained product is brought into contact with the novel transition metal compound.

Among these contacting methods, (I) and (II) are especially preferable. In any contacting method, components are brought into contact in the atmosphere of an inert gas such as nitrogen or argon usually, and in the presence of aromatic hydrocarbon (generally having 6 to 12 carbon atoms) such as benzene, toluene, xylene and ethyl benzene, otherwise in the presence of an inert liquid hydrocarbon of aliphatic or alicyclic hydrocarbon (generally having 5 to 12 carbon atoms) such as heptane, hexane, decane, dodecane or cyclohexane, with or without stirring.

There is no limitation concerning the ratios of the novel transition metal compound, organoaluminum compound and the carrier to be used. However, the following ratios are desirable.

The amount of the novel transition metal compound supported on 1 g of the layered silicate is 0.0001 to 5 mmol, preferably 0.001 to 0.5 mmol, and more preferably 0.01 to 0.1 mmol.

In the case that organoaluminum compound is used, the amount of supported aluminum is 0.01 to 100 mol, preferably 0.1 to 50 mol, and more preferably 0.2 to 10 mol.

In the process of the supporting and the removal of solvent, the same conditions as those in the forgoing inorganic carrier can be applied.

The thus obtained catalyst for olefin polymerization can be used, if necessary, after pre-polymerization of monomer.

The above-mentioned catalyst for polymerization is used for homopolymerization and copolymerization of olefins. These olefins herein referred to include α-olefins, cycloolefins, dienes, trienes, styrene analogs and olefins containing polar groups.

Included in the α-olefins are compounds each having 2 to 12 carbon atoms, preferably 2 to 8 carbon atoms. More particularly, ethylene, propylene, 1-butene, 1-hexene and 4-methyl-1-pentene are exemplified. By the used of the catalyst components of the present invention, the copolymerization of two or more α-olefins is carried out in addition to the homopolymerization. The copolymerization is any one of alternating copolymerization, random copolymerization and block copolymerization. The copolymerization of α-olefins includes the reaction of ethylene with α-olefin having carbon atoms of 3 to 12, preferably 3 to 8, such as ethylene with propylene, ethylene with 1-butene, ethylene with 1-hexene and ethylene with 4-methyl-1-pentene, and the reaction of propylene with α-olefin having carbon atoms of 3 to 12, preferably 3 to 8, such as propylene with 1-butene, propylene with 4-methyl-1-pentene, propylene with 1-hexene and propylene with 1-octene. In the copolymerization of ethylene or propylene with other α-olefin, the amount of other α-olefin can be selected from the range of 90 mol % or less in total amount of monomers. However, in-the copolymerization with ethylene, the amount is generally selected from the range of 40 mol % or less, preferably 30 mol % or less, and more preferably 20 mol % or less. In the copolymerization with propylene, the amount of other α-olefin is selected from the range of 1 to 90 mol %, preferably 5 to 90 mol %, and more preferably 10 to 70 mol %.

As the cycloolefins, the compounds having carbon atoms of 3 to 24, preferably 3 to 18, can be used in the present invention. The cycloolefins are exemplified by cyclopropene, cyclobutene, cyclopentene, cyclohexene, 3-methylcyclohexene, cyclooctene, cyclodecene, cyclododecene, tetracyclodecene, octacyclodecene, dicyclopentadiene, norbornene, 5-methyl-2-norbornene, 5-ethyl-2-norbornene, 5-isobutyl-2-norbornene, 5,6-dimethyl-2-norbornene, 5,5,6-trimethyl-2-norbornene and ethylidenenorbornene. The cycloolefin is usually copolymerized with the above-mentioned α-olefin. Their contents in the copolymer is in the range of 50 mol % or less, generally 1 to 50 mol %, and preferably 2 to 50 mol %.

As the dienes and the trienes, the compounds having carbon atoms of 4 to 24, preferably 4 to 18, can be used in the present invention. They are exemplified by butadiene, 1,4-hexadiene, 1,5-hexadiene, 1,9-decadiene, 1,13-tetradecadiene, 2,6-dimethyl-1,5-heptadiene, 2-methyl-2,7-octadiene, 2,7-dimethyl-2,6-octadiene and 1,5,9-decatriene. When chain diene or chain triene is used in the present invention, it is generally copolymerized with the above-mentioned α-olefin. The contents of the chain diene and/or the chain triene in the copolymer is generally in the range of 0.1 to 50 mol %, and preferably 0.2 to 10 mol %.

The styrene analogs usable in the present invention are styrene or styrene derivatives. The styrene derivatives are exemplified by t-butylstyrene, α-methylstyrene, p-methylstyrene, divinylbenzene, 1,1-diphenylethylene, N,N-dimethyl-p-aminoethylstyrene and N,N-diethyl-p-aminoethylstyrene.

The reaction of the polymerization is carried out by slurry polymerization, solution polymerization or gas-phase polymerization in the presence of the above-mentioned catalyst.. Among these methods, the slurry polymerization and the solution polymerization are preferable. In these polymerization processes, olefins are polymerized without the substantial existence of oxygen and water, and with or without the presence of an inert hydrocarbon solvent that is selected from aliphatic hydrocarbon such as isobutane, hexane or heptane; aromatic hydrocarbon such as benzene, toluene or xylene, and alicyclic hydrocarbon such as cyclohexane or methylcyclohexane. The conditions for the polymerization are such that the temperature is in the range of 20 to 200° C., preferably 50 to 100° C.; the pressure is in the range of normal pressure to 7 MPa, preferably normal pressure to 3 MPa; and the reaction time is 5 minutes to 10 hours, preferably 5 minutes to 5 hours.

The molecular weight of produced polymer can be adjusted to some extent by changing the conditions of polymerization temperature and molar ratios of components of catalyst. However, it is more effective for adjusting the molecular weight to supply hydrogen into the reaction system.

Even when a component for removal of water, called as scavenger, is supplied to the reaction system, the polymerization can be carried out without causing any difficulty. Preferable compounds as the scavenger are exemplified by organoaluminum compound such as trimethylaluminum, triethylaluminum and triisobutylaluminum; the above-mentioned organoaluminum oxy compounds, modified organoaluminum compounds having branched alkyl groups, organozinc compounds such as diethylzinc or dibutylzinc; organomagnesium compounds such as diethylmagnesium, dibutylmagnesium or ethylbutylmagnesium; and Grignard compounds such as ethylmagnesiumchloride or butylmagnesiumchloride. Among these compounds, triethylaluminum, triisobutylaluminum and ethylbutylmagnesium are more preferable, and triethylaluminum is most preferable.

They can be used also without any obstacle in the multistage polymerization of two or more stages, in which conditions of hydrogen concentrations, amounts of monomers, pressures and temperatures are different from one another.

BEST MODE FOR CARRYING OUT THE INVENTION

The present invention is described in more detail with reference to examples in the following. However, the present invention is not limited to these examples.

The properties of polymers obtained in examples and comparative examples were measured according to the following methods.

<Measurement of Melting Point by Differential Scanning Calorimeter (DSC)>

A melting point measuring apparatus of model: DSC 6200 R made by Seiko Instruments Inc. was used. A sample of 5 mg was maintained at 180° C. for 3 minutes, and then it was cooled to 0° C. at a rate of 10° C./minute. Subsequently, after maintaining the sample at 0° C. for 10 minutes, the melting point of the sample was measured by heating it at a rate of 10° C./minute.

<Measurement of Molecular Weight and Molecular Weight Distribution by GPC (Gel Permeation Chromatography)>

In order to measure molecular weight distribution, GPC apparatus of Alliance GPC 2000 made by Waters Corp. with a column of Shodex HT-806M was used by using a solvent of 1,2,4-trichlorobenzene. The temperature was 140° C. and the flow rate of the solvent was 1.0 ml per minute.

<Melt Index (MI)>

MI was measured according to ASTM D 1238-57T with a load of 2.16 kg at 190° C.

EXAMPLE 1

Under nitrogen atmosphere, 1 mmol (0.39 g) of bisindenylzirconium-dichloride ($Ind_2ZrCl_2$) was suspended in 30 ml of toluene in a 100 ml eggplant type flask. After cooling the contents to −78° C. with a freezing mixture (dry ice-ethanol), 2 mmol of n-butyllithium (n-BuLi) was added. The flask containing the mixed solution was taken out from the freezing mixture and the temperature was allowed to rise slowly. Subsequently, at a temperature of about 0° C., 4 mmol of indene was added. The temperature was further allowed to rise to room temperature and the contents were subjected to reaction for 30 minutes. After the reaction, the precipitated lithiumchloride (LiCl) was filtered off. The filtrate was subjected to reaction again at a temperature of 50° C. for 12 hours. Subsequently, the precipitate generated in this reaction was rinsed with n-hexane, and $Ind_3ZrH$ was obtained in a yield of 64%. The structure of this compound was determined by $^1H$-NMR, $^{13}C$-NMR and X-ray diffractometer.

Representative peaks of NMR spectrum were:

$^1H$-NMR (THF-$d_8$, $Me_4Si$): δ 2.03 (t, 3H), 2.95 (s, 1H), 5.79 (br, 6H), 6.97 (m, 6H), 7.34(m, 6H);

$^{13}C$-NMR (THF-$d_8$, $Me_4Si$): δ 90.12, 115.77, 123.51, 124.37, 131.36

Figure 1:
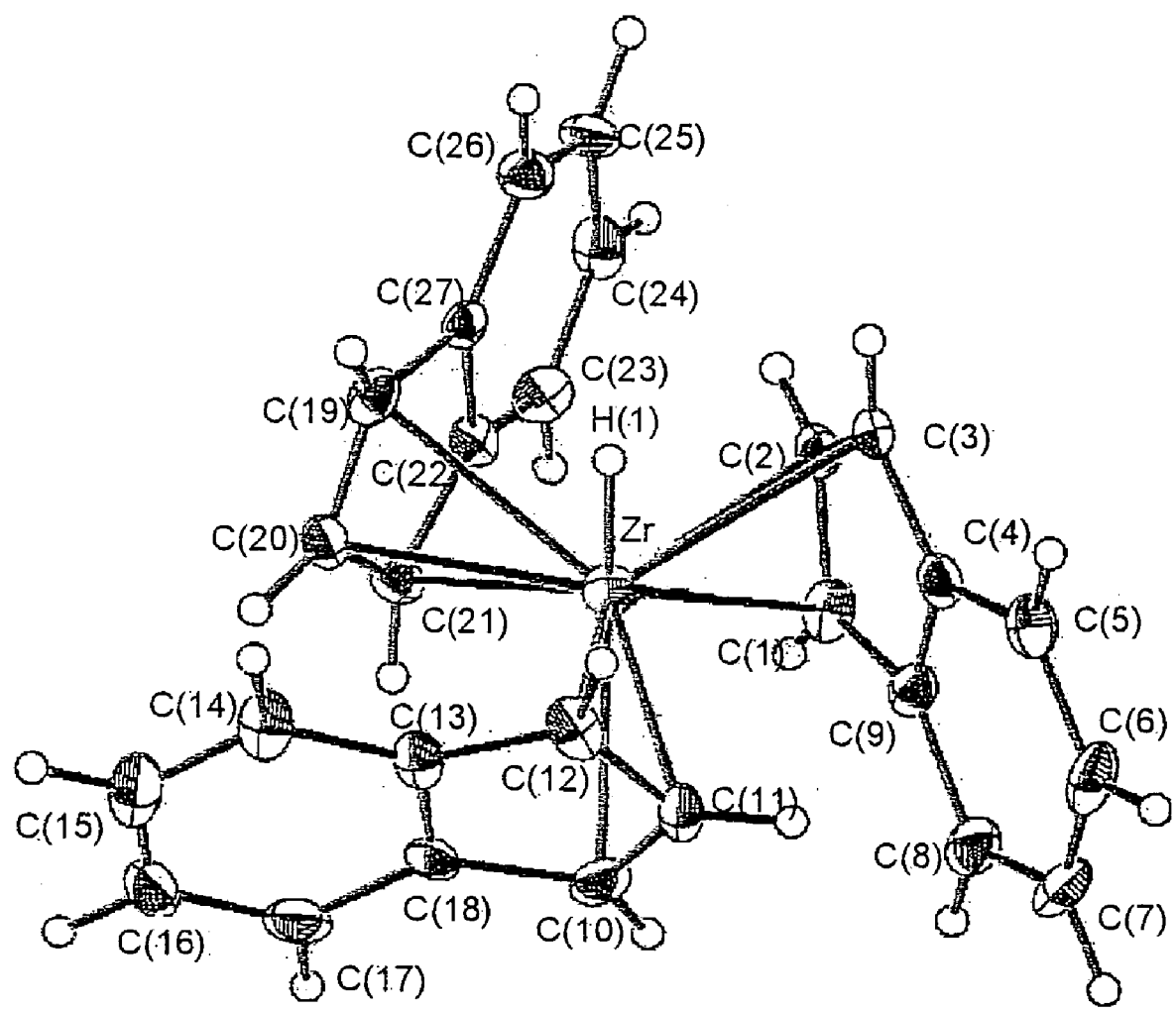
FIG. 1 is a drawing of the structure of the compound synthesized in Example 1, which is obtained by the processing of an electronic computer on the data of X-ray diffractometry.

The structure of the compound obtained by Example 1 is shown in FIG. 1, which was obtained by the processing of an electronic computer on the data of X-ray diffractometry.

EXAMPLE 2

Under nitrogen atmosphere, 1 mmol (0.29 g) of biscyclopentadienyl-zirconiumdichloride ($CP_2ZrCl_2$) was dissolved into 30 ml of toluene in a 100 ml eggplant type flask. After the solution was cooled to −78° C. with a freezing mixture (dry ice-ethanol), 2 mmol of n-butyllithium (n-BuLi) was added. The flask containing the solution mixture was taken out from the freezing mixture and the temperature was allowed to rise slowly. At a temperature of about 0° C., 4 mmol of methylcyclopentadiene was added. The temperature of the mixture was allowed to rise to room temperature and the contents were subjected to reaction for 30 minutes. After the reaction, precipitated lithiumchloride (LiCl) was filtered off. The filtrate was subjected to reaction again at 50° C. for 12 hours. Subsequently, the precipitate generated by this reaction was rinsed with n-hexane, and $(MeCp)(Cp)_2$ZrH was obtained in a yield of 70%. The structure of the compound was determined by $^1$H-NMR and $^{13}$C-NMR.

Representative peaks of NMR spectrum were:

$^1$H-NMR ($C_6D_6$, $Me_4Si$): δ 2.17(s, 3H), 2.98(s, 1H), 4.79(t, 2H), 5.31(t, 2H), 5.34(s, 10H);

$^{13}$C-NMR($C_6D_6$, $Me_4Si$): δ 16.38, 102.55, 105.43, 110.04, 118.50

EXAMPLE 3

Under nitrogen atmosphere, 1 mmol (0.29 g) of biscyclopentadienylzirconiumdichloride ($Cp_2ZrCl_2$) was dissolved into 30 ml of toluene in a 100 ml eggplant type flask. After the solution was cooled to −78° C. with a freezing mixture (dry ice-ethanol), 2 mmol of n-butyllithium (n-BuLi) was added. The flask containing the solution mixture was taken out from the freezing mixture and allowed the temperature to rise slowly. At a temperature of about 0° C., 4 mmol of trimethylsilylcyclopentadiene was added. The temperature of the mixture was allowed to rise to room temperature and the contents were subjected to reaction for 30 minutes. After the reaction, the precipitated lithiumchloride (LiCl) was filtered off. The filtrate was subjected to reaction again at a temperature of 80° C. for 3 hours. After the removal of solvent, precipitate generated in this reaction was rinsed with n-hexane and $(Me_3SiCp)(Cp)_2ZrH$ was obtained in a yield of 87%. The structure of the compound was determined by $^1$H-NMR.

Representative peaks of NMR spectrum were:

1H-NMR ($C_6D_6$, $Me_4Si$): δ 0.40 (s, 9H), 2.65 (s, 1H), 4.48 (t, 2H), 5.29 (s, 10H), 5.67 (t, 2H)

EXAMPLE 4

Under nitrogen atmosphere, 1 mmol (0.44 g) of trisindenylzirconiumhydride ($Ind_3ZrH$) obtained in Example 1 was suspended in 30 ml of toluene in a 100 ml eggplant type flask. Then, 8 mmol of trimethylsilylcyclopentadiene was added. After the mixture was subjected to reaction at 80° C. for 3 hours, the solvent was removed and solid precipitate was rinsed with n-hexane. Subsequently, $(Me_3SiCp)_3ZrH$ was obtained in a yield of 88%. The structure of the compound was determined by $^1$H-NMR and $^{13}$C-NMR.

Representative peaks of NMR spectrum were:

$^1$H-NMR ($C_6D_6$, $Me_4Si$): δ 3.35 (s, 1H), 4.83 (t, 6H), 5.86 (t, 6H);

$^{13}$C-NMR ($C_6D_6$, $Me_4Si$): δ 106.28, 110.10, 116.08

EXAMPLE 5

Under nitrogen atmosphere, 1 mmol (0.44 g) of trisindenylzirconiumhydride ($Ind_3ZrH$) obtained in Example 1 was suspended in 30 ml of toluene in a 100 ml eggplant type flask. And 8 mmol of methylcyclopentadiene was added. After the mixture was subjected to reaction at 80° C. for 3 hours, the solvent was removed and solid precipitate was rinsed with n-hexane. Subsequently, $(MeCp)_3ZrH$ was obtained in a yield of 87%. The structure of the compound was determined by $^1$H-NMR and $^{13}$C-NMR.

Representative peaks of NMR spectrum were:

$^1$H-NMR ($C_6D_6$, $Me_4Si$): δ 2.68 (s, 9H), 3.25 (s, 1H), 4.85 (t, 6H), 5.40 (t, 6H);

$^{13}$C-NMR ($C_6D_6$, $Me_4Si$): δ 16.41, 103.19, 110.52, 119.16

EXAMPLE 6

Under nitrogen atmosphere, 1 mmol (0.44 g) of trisindenyl-zirconiumhydride ($Ind_3ZrH$) obtained in Example 1 was suspended in 30 ml of toluene in a 100 ml eggplant type flask. And 8 mmol of 1,3-dimethyl-cyclopentadiene was added. After the mixture was subjected to reaction at 80° C. for 3 hours, the solvent was removed and solid precipitate was rinsed with n-hexane. Subsequently, $(1,3-Me_2Cp)_3ZrH$ was obtained in a yield of 80%. The structure of the compound was determined by $^1$H-NMR and $^{13}$C-NMR.

Representative peaks of NMR spectrum were:

$^1$H-NMR ($C_6D_6$, $Me_4Si$): δ 2.25 (s, 18H), 3.48 (s, 1H), 4.60 (t, 3H), 4.93 (d, 6H);

$^{13}$C-NMR ($C_6D_6$, $Me_4Si$): δ 15.90, 108.41, 115.36, 118.00

Figure 2:
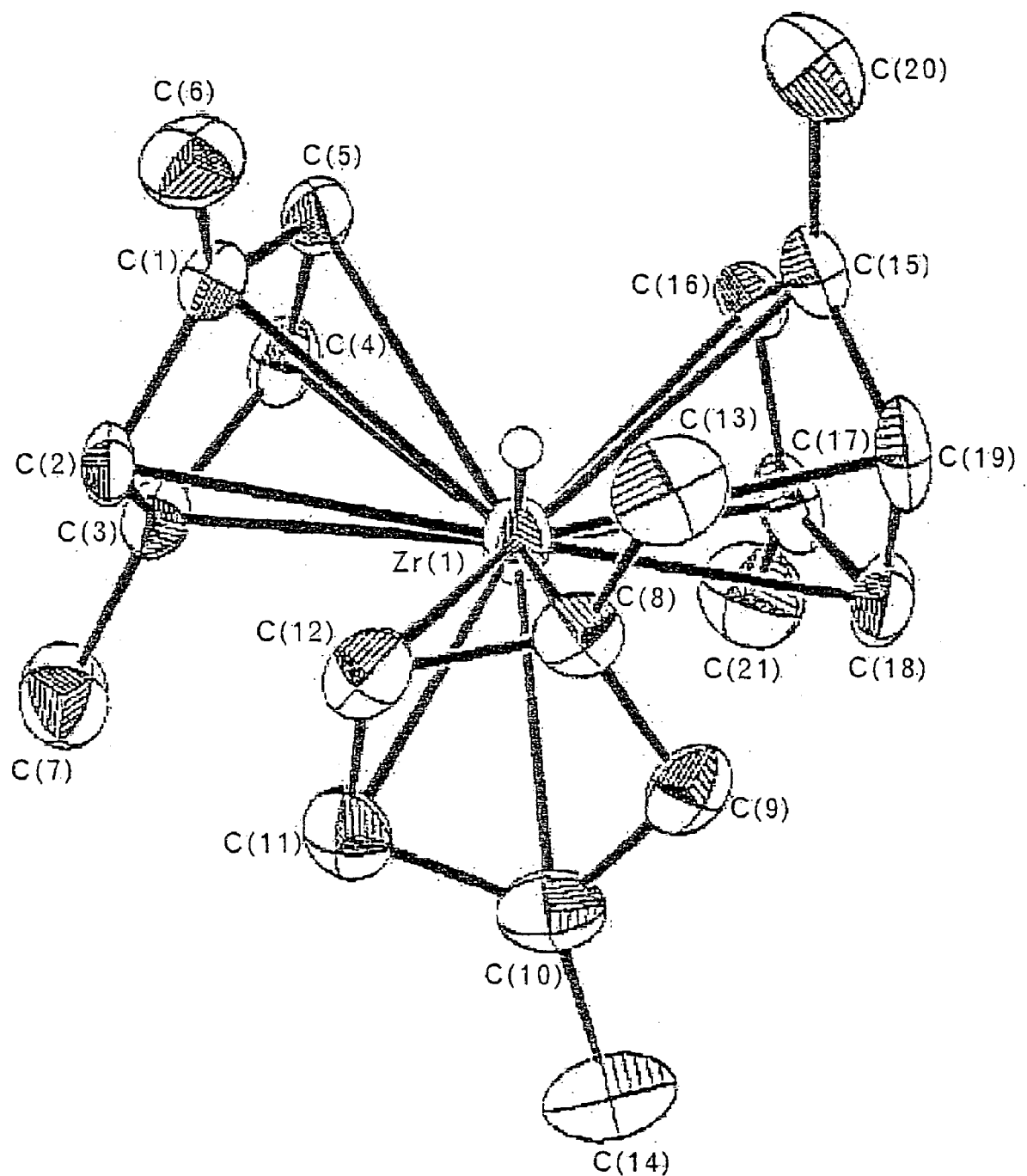
FIG. 2 is also a drawing of the structure of the compound synthesized in Example 6, which is obtained by the processing of an electronic computer on the data of X-ray diffractiometry.

The structure of the compound obtained in Example 6 is shown in FIG. 2, which was obtained by the processing of an electronic computer on the data of X-ray diffractiometry

EXAMPLE 7

Under nitrogen atmosphere, 0.42 mmol (0.185 g) of trisindenylzirconiumhydride ($Ind_3ZrH$) obtained in Example 1 was suspended in 8.4ml of toluene in a 50 ml eggplant type flask. After 1.68 mmol of 1,3-dimethylcyclopentadiene was added, the mixture was subjected to reaction at 40° C. for 48 hours. Subsequently, $Ind(1,3-Me_2Cp)_2ZrH$ was obtained. The yield was determined by $^1$H-NMR was 50%.

Representative peaks of NMR spectrum were.

$^1$H-NMR ($C_6D_6$, $Me_4Si$): δ 3.56 (s, 1H), 4.23 (t, 2H), 4.42 (t, 2H), 4.57 (t, 2H)

EXAMPLE 8

Under nitrogen atmosphere, 2.9 mmol (1.27 g) of trisindenylzirconiumhydride ($Ind_3ZrH$) obtained in Example 1 was suspended in 30 ml of toluene in a 50 ml eggplant type flask. Then, 11.6 mmol of 1-methyl-3-propylcyclopentadiene was added and subjected to reaction at 80° C. for 2 hours. The solvent was then removed and solid precipitate was rinsed with n-hexane. Subsequently, $(1-Me-3-PrCp)_3ZrH$ was obtained in a yield of 90%.

The structure of the compound was determined by $^1$H-NMR.

Representative peaks of NMR spectrum were:

$^1$H-NMR ($C_6D_6$, $Me_4Si$): δ 0.96 (t, 9H), 2.27 (t, 9H), 3.41 (s, 1H), 4.63 (s, 3H), 4.90 (m, 3H), 4.96 (m, 3H)

EXAMPLE 9

Under nitrogen atmosphere, 0.31 mmol (0.14 g) of tris-indenylzirconiumhydride ($Ind_3ZrH$) obtained in Example 1 was suspended in 5 ml of hexane in a 50 ml eggplant type flask. Then, 1.2 mmol of benzoindene (BenzInd) was added and the mixture was subjected to reaction at 50° C. for 2 hours. After the solvent was removed, solid precipitate was rinsed with n-hexane. Subsequently, $(BenzInd)_3ZrH$ was obtained in a yield of 83%. The structure of the compound was determined by $^1$H-NMR.

Representative peaks of NMR spectrum were:

$^1$H-NMR ($C_6D_6$, $Me_4Si$): δ 3.30 (t, 3H), 3.85 (s, 1H), 5.80 (s, 3H), 5.97 (s, 3H), 7.25 (t, 3H), 7.35 (t, 3H), 7.66 (d, 3H), 7.51(d, 3H)

EXAMPLE 10

Under nitrogen atmosphere, 21 ml of toluene solution containing 0.1 mol of dibenzoindene per 1 liter of toluene was added to 0.64 mmol (0.28 g) of trisindenylzirconium-hydride ($Ind_3ZrH$) obtained in Example 1 to form a suspension in a 50 ml eggplant type flask. The suspension was subjected to reaction at 80° C. for 30 minutes. (After the suspension turned into a uniform solution by heating, solid precipitate was generated.) After filtration and rinsing with n-pentane, 0.38 g of precipitate was collected. The precipitate was decomposed with methanol and was subjected to $^1$H-NMR, as a result only dibenzoindene was confirmed. In view of the amount of dibenzoindene formed by the decomposition, it was understood that the solid substance obtained by the reaction was $(DibenzoInd)_3ZrH$. The yield was 81%.

EXAMPLE 11

The following polymerization was carried out using $Ind_3ZrH$ obtained in Example 1 as a component of catalyst.

Into a 20 ml Schlenk tube that was purged with nitrogen gas, 5 ml of toluene, 5.0 μmol of a compound of $Ind_3ZrH$ and 5.0 mmol of toluene solution containing MAO (2.6 mmol/ml) were added together at room temperature, and the mixture was stirred for 5 minutes.

Toluene of 100 ml was supplied into a 200 ml stainless steel autoclave, which was equipped with a stirrer and was replaced with nitrogen gas in advance. Subsequently, 1.4 ml of the above-mentioned catalyst solution was added and heated to 80° C. with stirring. Then, ethylene was fed into the autoclave to make the pressure 0.6 MPa so as to start polymerization. The polymerization was continued for 5 minutes and was then stopped by feeding ethanol.

Polyethylene was obtained through the polymerization. The polymerization activity was 74 kg PE/(mmol Zr-MPa-h). The polyethylene had the properties of 102,600 in Mw and 2.97 in Mw/Mn.

EXAMPLE 12

By using $Ind_3ZrH$ obtained in Example 1 as catalyst, the following polymerization process was carried out.

A 100 ml flask was fed with 0:4 mmol of $Ind_3ZrH$ obtained in Example 1 under nitrogen atmosphere. Then, 15 ml of toluene was added to generate a toluene suspension. Subsequently, 40 mmol of a solution of methylaluminoxane (concentration of 2.6 mmol/ml (number of moles of Al atom) was added and the mixture was stirred at room temperature for 10 minutes.

Into a 300 ml flask, 10 g of $SiO_2$ sintered at 400° C. for 5 hours and the whole amount of the above-mentioned solution were added. The solvent was removed by nitrogen gas blowing and pressure reduction, a solid of catalyst component with fluidity was obtained.

A 2.7 lit. stainless steel autoclave, which was equipped with a stirrer, kept at 75° C. and replaced with nitrogen gas was used. Into this autoclave was added 0.25 ml of hexane solution of triethylaluminum (0.5 mmol/ml) and 130 mg of the above-mentioned solid catalyst. The polymerization was then carried out for two hours with adjusting the molar ratio of 1-butene/ethylene in gas phase to 0.12 and the total pressure to 0.9 MPa with feeding every gas.

The polymerization activity was 1730 g/(g catalyst-MPa-h). The obtained ethylene copolymer had properties of 1.4 g/10 minutes in MI, 0.9248 g/cm$^3$ in density, 124,500 in Mw, 2.5 in Mw/Mn, 0.42 g/cm$^3$ in bulk density and 118.1° C. in melting point.

EXAMPLE 13

By using a compound of $(1,3-Me_2CP)_3ZrH$ obtained in Example 6, the polymerization was carried out as follows.

Into a 20ml Schlenk tube purged with nitrogen gas, 5 ml of toluene, 5.0 μmol of the compound of $(1,3-Me_2CP)_3ZrH$ and 5.0 mmol of toluene solution containing MAO (2.6 mmol/ml) were fed at room temperature, and the mixture was stirred for 1 minute.

A 200 ml stainless steel autoclave equipped with a stirrer was replaced with nitrogen gas and fed with 100 ml of toluene. Subsequently, 1.4 ml of the above-mentioned solution containing catalyst was added and it was heated to 80° C. with stirring. Ethylene was then fed into the autoclave so as to keep the pressure of 0.6 MPa and to start polymerization. The polymerization was carried out for 5 minutes. The polymerization was stopped by the feeding of ethanol.

Polyethylene was obtained by the polymerization. The polymerization activity was 60 kg PE/(mmol Zr—MPa—h).

EXAMPLE 14

By using the compound of $(Me_2CP)_3ZrH$ obtained in Example 6, polymerization was carried out as follows.

Under nitrogen atmosphere, a 100 ml flask was fed with 0.2 mmol of $(Me_2CP)_3ZrH$ obtained in Example 6, and with 15 ml of toluene to form a toluene suspension. Subsequently, 40 mmol of methylaluminoxane solution of a concentration of 2.9 mmol/ml (moles of Al atom) was added and it was stirred at room temperature for 10 minutes.

A 300 ml flask was fed with 10 g of $SiO_2$ that was sintered at 650° C. for 5 hours, and the whole amount of the above-mentioned solution was added. The solvent was removed by nitrogen gas blowing and by reduced pressure, a fluidizable solid of catalyst component was obtained.

A 2.7 lit. stainless steel autoclave equipped with a stirrer was replaced with nitrogen gas and maintained at 75° C., and it was fed with 0.3 ml of hexane solution of triethylaluminum (0.5 mmol/ml) and 70 mg of the above-mentioned solid catalyst. Polymerization was carried out for two hours with adjusting the molar ratio of 1-butene/ethylene in the gas phase to 0.08, hydrogen concentration to 600 ppm and total pressure to 0.9 MPa by feeding the respective gases.

The polymerization activity was 350 g PE/(g catalyst-MPa-h). The obtained ethylene copolymer had the properties of 0.23 g/10 minutes in MI, 0.9160 g/cm$^3$ in density, 140,000 in Mw, 3.4 in Mw/Mn and 0.38 g/cm$^3$ on bulk density.

EXAMPLE 15

By using a compound of (BenzInd)$_3$ZrH obtained in Example 9, the polymerization was carried out as follows.

A 100 ml flask was fed with 0.2 mmol of (BenzInd)$_3$ZrH obtained in Example 9, under nitrogen atmosphere, and 15 ml of toluene was added to form a toluene suspension. Subsequently, 40 mmol of methylaluminoxane solution of a concentration of 2.9 mmol/ml (moles of Al atom) was added and the mixture was stirred at room temperature for 10 minutes.

A 300 ml flask was fed with 10 g of SiO$_2$ that was sintered at 650° C. for 5 hours. The whole amount of the above-mentioned solution. was added. Subsequently, after the solvent was removed by nitrogen gas blowing and by reduced pressure, a fluidizable solid of catalyst component was obtained.

A 2.7 lit. stainless steel autoclave equipped with a stirrer was replaced with nitrogen gas and was maintained at 75° C. It was fed with 0.3 ml of a hexane solution of triethylaluminum (0.5 mmol/ml) and 90 mg of the above-mentioned solid catalyst. Polymerization was carried out for two hours with adjusting the molar ratio of 1-butene/ethylene in the gas phase to 0.08, hydrogen concentration to 700 ppm and total pressure to 0.9 MPa by feeding the respective gases.

The polymerization activity was 200 g PE/(g catalyst-MPa-h). The obtained ethylene copolymer had properties of 0.52 g/10 minutes in MI, 0.9200 g/cm$^3$ in density, 100,000 in Mw, 3.2 in Mw/Mn and 0.39 g/cm$^3$ in bulk density.

EXAMPLE 16

By using a compound of Ind$_3$ZrH obtained in Example 1, the polymerization was carried out as follows.

To a 50 ml flask were added, under nitrogen atmosphere, 0.2 mmol of Ind$_3$ZrH obtained in Example 1 and 10 ml of toluene to form a toluene suspension. Subsequently, 8.7 mmol of triisobutylaluminum solution (Al: 10 mmol) of a concentration of 1.15 mmol/ml (moles of Al atom) was added and the mixture was stirred at room temperature for 10 minutes.

A 300 ml flask was fed with 10 g of layered silicate and, after drying in vacuum at 180° C., the whole amount of the above-mentioned solution was added. Subsequently, after the solvent was removed by nitrogen gas blowing and by reduced pressure, fluidizable solid of catalyst component was obtained.

A 2.7 lit. stainless steel autoclave was equipped with a stirrer was replaced with nitrogen gas and maintained at 75° C. It was fed with 900 ml of hexane, 1.0 ml of hexane solution of triisobutylaluminum (0.1 mmol/ml), 15 ml of 1-hexene and 130 mg of the above-mentioned solid catalyst and polymerization was carried out for two hours with adjusting the total pressure to 0.9 MPa with feeding ethylene.

The polymerization activity was 1730 g/(g catalyst-MPa-h). The obtained ethylene copolymer had properties of 0.9 g/10 minutes in MI, 0.9269 g/cm$^3$ in density, 132,600 in Mw, 2.2 on Mw/Mn and 0.42 g/cm$^3$ in bulk density.

COMPARATIVE EXAMPLE 1

The polymerization was carried out by using Ind$_2$ZrCl$_2$ as a catalyst component.

Into a 20 ml Schlenk tube purged by nitrogen gas, 5 ml of toluene, 5.0 μmol of Ind$_2$ZrCl$_2$ and 5.0 mmol of toluene solution containing MAO(2.6 mmol/ml) were added at room temperature, and the mixture was stirred for 30 minutes.

A 200 ml stainless steel autoclave that was equipped with a stirrer and replaced with nitrogen gas, was fed with 100 ml of toluene and 1.4 ml of the above-mentioned catalyst solution. The mixture was heated to 80° C. with stirring. Polymerization was carried out for 5 minutes with adjusting the pressure to 0.6 MPa by feeding ethylene. The polymerization was stopped by feeding ethanol.

Polyethylene was obtained by the polymerization, in which the polymerization activity was 43 kg PE/(mmol Zr-MPa-h).

COMPARATIVE EXAMPLE 2

The polymerization was carried out by using Ind$_2$ZrCl$_2$.

A 100 ml flask under nitrogen atmosphere, 0.4 mmol of Ind2ZrCl$_2$ and 15 ml of toluene was added to form a toluene suspension. Subsequently, 40 mmol of methylaluminoxane solution of concentration of 2.6 mmol/ml (moles of Al atom) was added and the mixture was stirred at room temperature for 10 minutes.

A 300 ml flask was fed with 10 g of SiO$_2$ that was sintered at 400° C. for 5 hours and the whole amount of the above-mentioned solution.

Subsequently, after the solvent was removed by nitrogen gas blowing and by reduced pressure, fluidizable solid catalyst component was obtained.

A 2.7 lit. stainless steel autoclave equipped with a stirrer was maintained at 75° C. and was replaced with nitrogen gas. It was fed with 0.25 ml of hexane solution of triethylaluminum (0.5 mmol/ml) and 130 mg of the above-mentioned solid catalyst. Polymerization was carried out for two hours with adjusting the molar ratio of 1-butene/ethylene in the gas phase to 0.12 and the total pressure to 0.9 MPa by feeding the respective gases.

The polymerization activity was 750 g/(g catalyst-MPa-h). The obtained ethylene copolymer had properties of 0.4 g/10 minutes in MI, 0.9148 g/cm$^3$ in density, 0.38 g/cm$^3$ in bulk density and 114.7° C. in melting point.

INDUSTRIAL APPLICABILITY

The present invention provides a novel transition metal compound, which has not hitherto been known. The novel transition metal compound can be used as the component of catalyst for olefin polymerization having excellent activity. Furthermore, the transition metal compound does not contain any halogen element, so that the olefin polymer obtained by using the catalyst does not contain halogen element, as a result, the amount of additives such as a stabilizer can be reduced.

What is claimed is:

1. A transition metal compound represented by the following general formula (2):

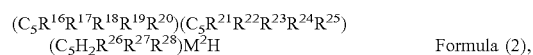

$$(C_5R^{16}R^{17}R^{18}R^{19}R^{20})(C_5R^{21}R^{22}R^{23}R^{24}R^{25})(C_5H_2R^{26}R^{27}R^{28})M^2H \quad \text{Formula (2)},$$

wherein $C_5R^{16}R^{17}R^{18}R^{19}R^{20}$, $C_5R^{21}R^{22}R^{23}R^{24}R^{25}$ and $CH^5H_2R^{26}R^{27}R^{28}$ denote cyclopentadienyl groups or substituted cyclopentadienyl groups, respectively;

$R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are any of hydrogen, a hydrocarbon group having a substituent of a hydrocarbon having 1 to 30 carbon atoms, which are the same or different;

among them, $R^{16}$, $R^{17}$, $R^{18}$, $R^{19}$, $R^{20}$, or $R^{21}$, $R^{22}$, $R^{23}$, $R^{24}$, $R^{25}$, or $R^{26}$, $R^{27}$, $R^{28}$ can be bonded to one another forming a cyclic hydrocarbon group, including a polycyclic structure;

provided that at least one of $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ is a substituent other than hydrogen; and $M^2$ denotes a transition metal of group 4 of the periodic table.

2. The transition metal compound as claimed in claim 1, wherein $R^{26}$, $R^{27}$ and $R^{28}$ are bonded to adjacent carbons at the 1-position, 2-position and 3-position.

3. The transition metal compound represented by the following general formula (3) as claimed in claim 1;

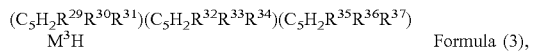

$$(C_5H_2R^{29}R^{30}R^{31})(C_5H_2R^{32}R^{33}R^{34})(C_5H_2R^{35}R^{36}R^{37})M^3H \quad \text{Formula (3)},$$

wherein $(C_5H_2R^{29}R^{30}R^{31})$, $(C_5H_2R^{32}R^{33}R^{34})$ and $(C_5H_2R^{35}R^{36}R^{37})$ denote cyclopentadienyl groups or substituted cyclopentadienyl groups, respectively;

$R^{29}$, $R^{30}$, $R^{31}$, $R^{32}$, $R^{33}$, $R^{34}$, $R^{35}$, $R^{36}$ and $R^{37}$ are any one of hydrogen, a hydrocarbon group having 1 to 30 carbon atoms or an organosilicon group having a substituent of a hydrocarbon having 1 to 30 carbon atoms, which are the same or different, among them, $R^{29}$, $R^{30}$, $R^{31}$, or $R^{32}$, $R^{33}$, $R^{34}$, or $R^{35}$, $R^{36}$, $R^{37}$, can be bonded to one another forming a cyclic hydrocarbon group, including a polycyclic structure;

provided that at least one of $R^{29}$, $R^{30}$, $R^{31}$, $R^{32}$, $R^{33}$, $R^{34}$, $R^{35}$, $R^{36}$ and $R^{37}$ is a substituent other than hydrogen; and $M^3$ denotes a transition metal of group 4 of the periodic table.

4. The transition metal compound as claimed in claim 3, wherein $R^{29}$, $R^{30}$, $R^{31}$, or $R^{32}$, $R^{33}$, $R^{34}$, or $R^{35}$, $R^{36}$, $R^{37}$ are bonded to adjacent carbon atoms at the 1-position, 2-position and 3-position of the respective cyclopentadienyl group.

5. The transition metal compound as claimed in claim 4, wherein the three substituted cyclopentadienyl groups of $(C_5H_2R^{29}R^{30}R^{31})$, $(C_5H_2R^{32}R^{33}R^{34})$ and $(C_5H_2R^{35}R^{36}R^{37})$ have the same structure.

6. The transition metal compound represented by the following general formula (4) as claimed in claim 1:

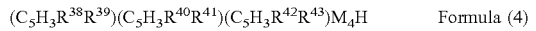

$$(C_5H_3R^{38}R^{39})(C_5H_3R^{40}R^{41})(C_5H_3R^{42}R^{43})M_4H \quad \text{Formula (4)}$$

wherein $(C_5H_3R^{38}R^{39})$, $(C_5H_3R^{40}R^{41})$ and $(C_5H_3R^{42}R^{43})$ denote cyclopentadienyl groups or substituted cyclopentadienyl groups, respectively:

$R^{38}$, $R^{39}$, $R^{40}$, $R^{41}$, $R^{42}$ and $R^{43}$ are any one of hydrogen, a hydrocarbon group having 1 to 30 carbon atoms or organosilicon group having a substituent of a hydrocarbon having 1 to 30 atoms, which are the same or different;

among them, $R^{38}$, $R^{39}$, or $R^{40}$, $R^{41}$, or $R^{42}$, $R^{43}$ can be bonded to one another forming a cyclic hydrocarbon group, including a polycyclic structure;

provided that at least one of $R^{38}$, $R^{39}$, $R^{40}$, $R^{41}$, $R^{42}$ and $R^{43}$ is a substituent other than hydrogen; and M4 denotes a transition metal of group 4 of the periodic table.

7. The transition metal compound as claimed in claim 6, wherein the three substituted cyclepentadienyl groups of $(C_5H_3R^{38}R^{39})$, $(C_5H_3R^{40}R^{41})$ and $(C_5H_3R^{42}R^{43})$ have the same structure.

8. The transition metal compound represented by the following general formula (5) as claimed in claim 1;

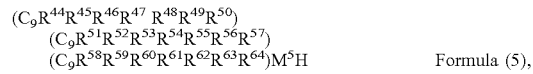

$$(C_9R^{44}R^{45}R^{46}R^{47}R^{48}R^{49}R^{50})(C_9R^{51}R^{52}R^{53}R^{54}R^{55}R^{56}R^{57})(C_9R^{58}R^{59}R^{60}R^{61}R^{62}R^{63}R^{64})M^5H \quad \text{Formula (5)},$$

wherein $(C_9R^{44}R^{45}R^{46}R^{47}R^{48}R^{49}R^{50})$, $(C_9R^{51}R^{52}R^{53}R^{54}R^{55}R^{56}R^{57})$ and $(C_9R^{58}R^{59}R^{60}R^{61}R^{62}R^{63}R^{64})$ denote indenyl groups or substituted indenyl groups, respectively;

$R^{44}$ to $R^{64}$ are any one of hydrogen, a hydrocarbon group having 1 to 30 carbon atoms or organosilicon group having a substituent of a hydrocarbon having 1 to 30 carbon atoms, which are the same or different, among them $R^{44}$ to $R^{50}$ or $R^{51}$ to $R^{57}$ or $R^{58}$ to $R^{64}$ can be bonded to one another forming a cyclic hydrocarbon group, including a polycyclic structure;

provided that at least one of $R^{38}$, $R^{39}$, $R^{40}$, $R^{41}$, $R^{42}$ and $R^{43}$ is a substituent other than hydrogen; and $M^5$ denotes a transition metal of group 4 of the period table.

9. The transition metal compound represented by the following general formula (6) as claimed in claim 1:

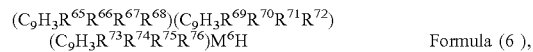

$$(C_9H_3R^{65}R^{66}R^{67}R^{68})(C_9H_3R^{69}R^{70}R^{71}R^{72})(C_9H_3R^{73}R^{74}R^{75}R^{76})M^6H \quad \text{Formula (6)},$$

wherein $(C_9H_3R^{65}R^{66}R^{67}R^{68})$, $(C_9H_3R^{69}R^{70}R^{71}R^{72})$ and $(C_9H_3R^{73}R^{74}R^{75}R^{76})$ denote indenyl groups or substituted indenyl groups, respectively;

$R^{65}$ to $R^{76}$ are any one of hydrogen, a hydrocarbon group having 1 to 30 carbon atoms or organosilicon group having a substituent of a hydrocarbon having 1 to 30 carbon atoms, which are the same or different;

among them, $R^{65}$ to $R^{68}$, $R^{69}$ to $R^{72}$ and $R^{73}$ to $R^{76}$ are be bonded to carbon atoms at the 4-position, 5-position, 6-position and 7-position, respectively, of the indenyl groups and they can be bonded to one another forming cyclic hydrocarbon groups, including a polycyclic structure; and $M^6$ denotes a transition metal of group 4 of the periodic table.

10. The transition metal compound as claimed in claim 9, wherein the three substituted indenyl groups of $(C_9H_3R^{65}R^{66}R^{67}R^{68})$, $(C_9H_3R^{69}R^{70}R^{71}R^{72})$ and $(C_9H_3R^{73}R^{74}R^{75}R^{76})$ have the same structure.

11. The transition metal compound as claimed in claim 1, wherein the transition metal of group 4 of the period table is Zr.

12. A catalyst for olefin polymerization, which comprises the transition metal compound as claimed in claim 1, an organoaluminum oxy compound and/or a compound that forms ion pairs with the transition metal compound.

13. The catalyst for olefin polymerization as claimed in claim 12, wherein the organoaluminum oxy compound is methyl aluminoxane.

14. A solid catalyst for olefin polymerization, wherein the catalyst as claimed in claim 12 is supported on a carrier.

15. A solid catalyst for olefin polymerization, wherein the transition metal compound as claimed in claim 1 is supported on a layered silicate.

16. A method for producing a polyolefin, wherein an olefin is polymerized in the presence of the catalyst as claimed in claim 12.

17. The method for producing a polyolefin as claimed in claim 16, wherein the olefin polymerization is homopolymerization of ethylene or copolymerization of ethylene and an α-olefin.

* * * * *